(12) United States Patent
Imai et al.

(10) Patent No.: US 10,086,152 B2
(45) Date of Patent: Oct. 2, 2018

(54) LIQUID ADMINISTRATION DEVICE

(71) Applicant: Terumo Kabushiki Kaisha, Tokyo (JP)

(72) Inventors: Masaomi Imai, Chuo (JP); Ruriko Iibuchi, Hadano (JP); Manabu Arinobe, Hadano (JP)

(73) Assignee: Terumo Kabushiki Kaisha, Tokyo (JP)

( * ) Notice: Subject to any disclaimer, the term of this patent is extended or adjusted under 35 U.S.C. 154(b) by 228 days.

(21) Appl. No.: 14/641,282

(22) Filed: Mar. 6, 2015

(65) Prior Publication Data

US 2015/0258283 A1    Sep. 17, 2015

(30) Foreign Application Priority Data

Mar. 11, 2014   (JP) .................................. 2014-047697

(51) Int. Cl.
| | |
|---|---|
| *A61M 5/24* | (2006.01) |
| *A61M 5/32* | (2006.01) |
| *A61M 5/20* | (2006.01) |
| *A61M 5/315* | (2006.01) |
| *A61M 5/50* | (2006.01) |

(52) U.S. Cl.
CPC ........ *A61M 5/3293* (2013.01); *A61M 5/2033* (2013.01); *A61M 5/31501* (2013.01); *A61M 5/3202* (2013.01); *A61M 5/326* (2013.01); *A61M 5/3243* (2013.01); *A61M 5/3271* (2013.01); *A61M 5/3272* (2013.01); *A61M 5/50* (2013.01); *A61M 2005/2013* (2013.01); *A61M 2005/3151* (2013.01);

(Continued)

(58) Field of Classification Search
CPC .............. A61M 5/2033; A61M 5/3271; A61M 2005/206; A61M 2005/2073; A61M 2005/3247; A61M 2005/3267
USPC ................ 604/135, 136, 157, 192, 197, 198
See application file for complete search history.

(56) References Cited

U.S. PATENT DOCUMENTS

| | | | |
|---|---|---|---|
| 6,277,099 B1 * | 8/2001 | Strowe .............. | A61M 5/31553 604/186 |
| 2004/0024367 A1 * | 2/2004 | Gilbert ................ | A61M 5/2033 604/198 |

(Continued)

FOREIGN PATENT DOCUMENTS

| | | |
|---|---|---|
| JP | 2013-508032 | 3/2013 |
| WO | WO-2009-040602 | 4/2009 |

OTHER PUBLICATIONS

European Search Report issued from EP application No. EP15 15 8373 dated Jul. 29, 2015.

*Primary Examiner* — Gerald Landry, II
(74) *Attorney, Agent, or Firm* — Foley & Lardner LLP

(57) ABSTRACT

A liquid administration device includes an operation unit; a structure that includes an accommodation body configured to accommodate the liquid therein and a needle tube communicatable with the inside of the accommodation body; a cover member that is movable between a protection position and an exposure position; a biasing member that biases the cover member in a distal direction; an exposure restriction unit configured to restrict movement of the cover member to the exposure position when a movement amount of the cover member with respect to the structure reaches a predetermined exposure restriction operation amount; and a movement amount restriction unit.

24 Claims, 21 Drawing Sheets

(52) U.S. Cl.
CPC ............ *A61M 2005/31508* (2013.01); *A61M 2005/3247* (2013.01); *A61M 2005/3267* (2013.01)

(56) References Cited

U.S. PATENT DOCUMENTS

| | | | | |
|---|---|---|---|---|
| 2004/0225262 A1* | 11/2004 | Fathallah | ............ | A61M 5/2033 604/198 |
| 2005/0273055 A1* | 12/2005 | Harrison | ............... | A61M 5/326 604/136 |
| 2009/0270804 A1* | 10/2009 | Mesa | ................... | A61M 5/2033 604/111 |
| 2011/0092915 A1 | 4/2011 | Olson et al. | | |
| 2011/0202011 A1* | 8/2011 | Wozencroft | ........ | A61M 5/2033 604/192 |
| 2011/0257603 A1* | 10/2011 | Ruan | ..................... | A61M 5/326 604/198 |
| 2011/0288491 A1* | 11/2011 | Newman | ............... | A61M 5/326 604/198 |
| 2012/0101475 A1* | 4/2012 | Wilmot | ............... | A61M 5/2033 604/506 |
| 2012/0184917 A1 | 7/2012 | Bom et al. | | |
| 2014/0207106 A1* | 7/2014 | Bechmann | .......... | A61M 5/2033 604/506 |
| 2014/0323982 A1* | 10/2014 | Lumme | ............... | A61M 5/3234 604/218 |
| 2015/0051578 A1* | 2/2015 | Herr | ........................ | A61M 5/24 604/506 |
| 2016/0193424 A1* | 7/2016 | Bayer | ................. | A61M 5/3157 604/211 |

* cited by examiner

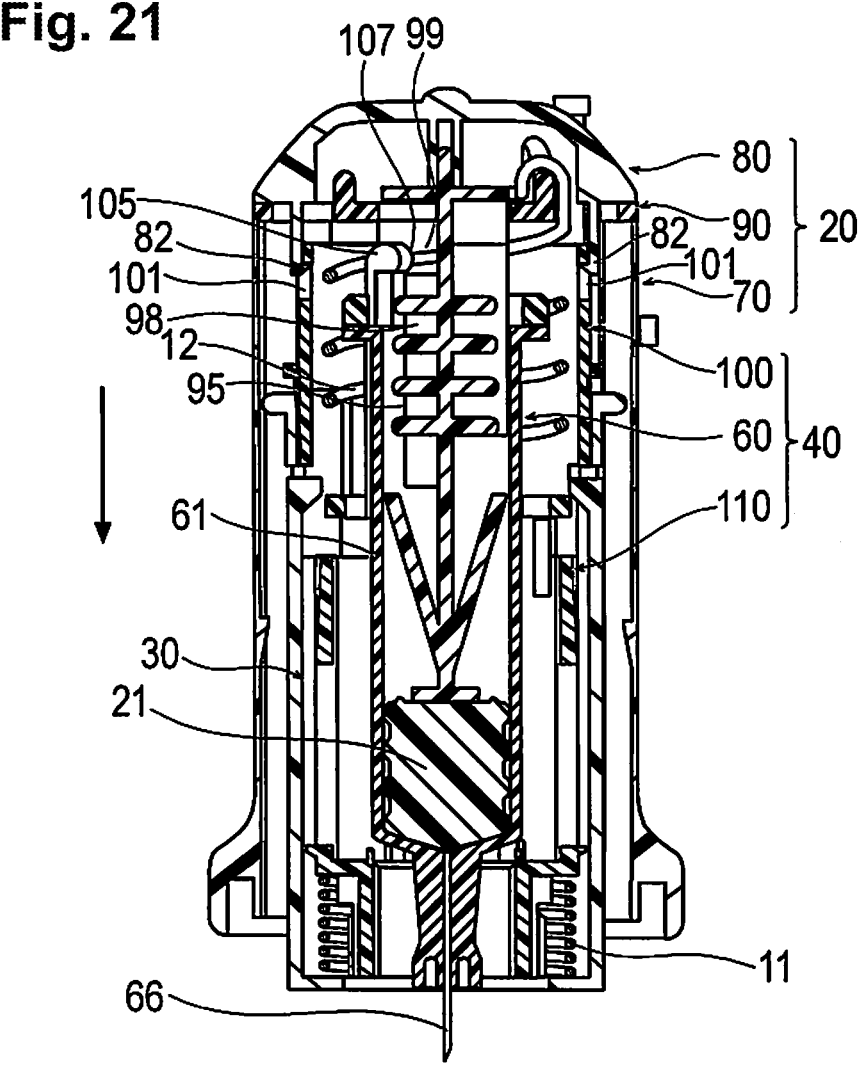

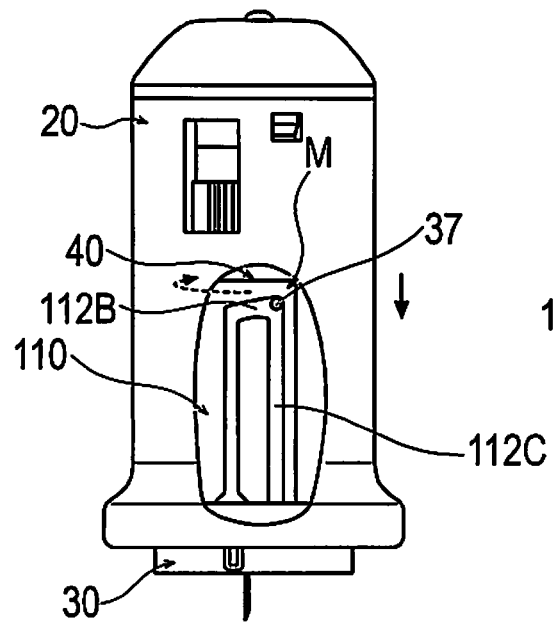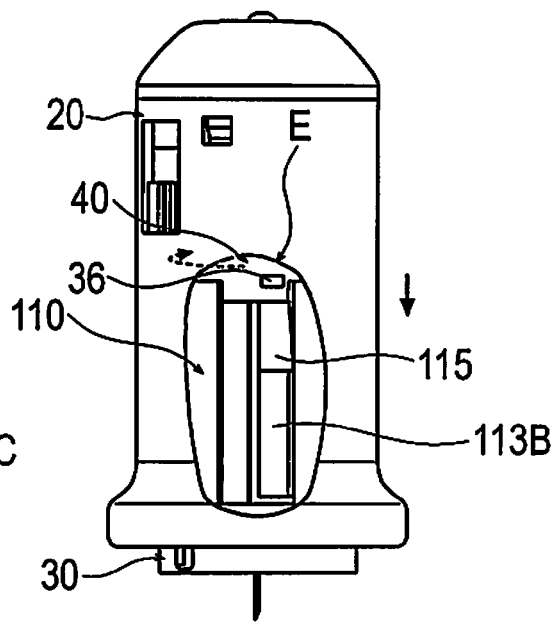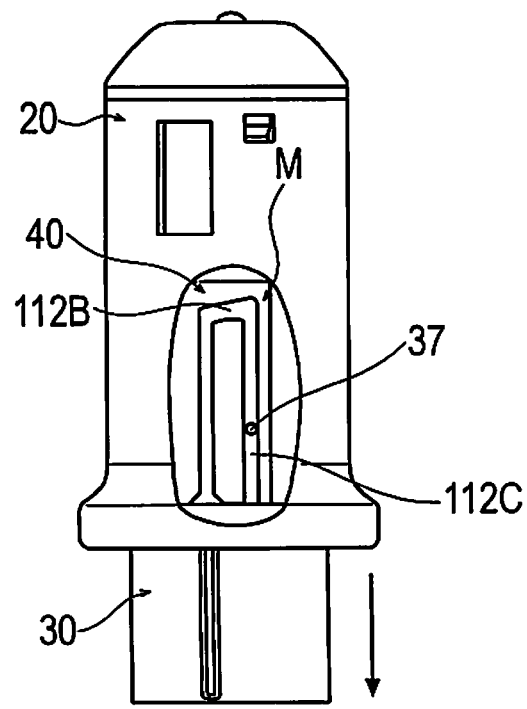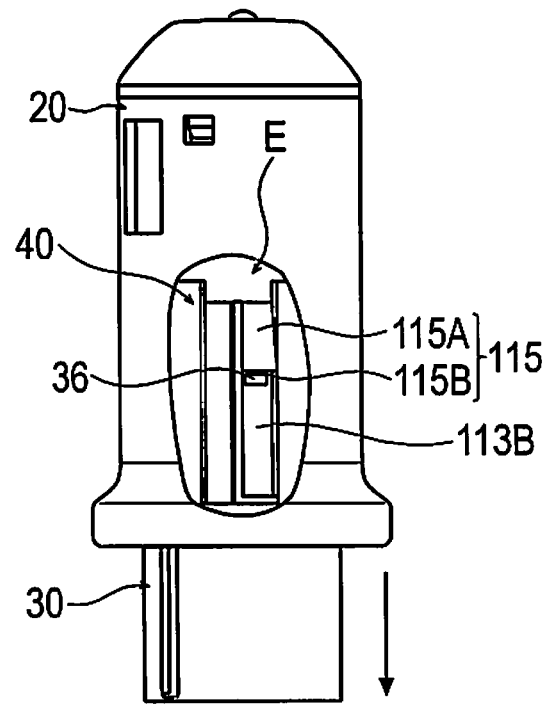

Fig. 27(A)
Fig. 27(B)
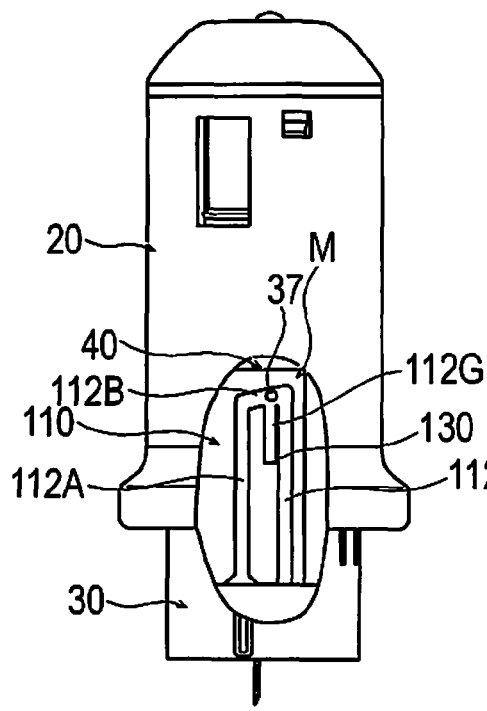
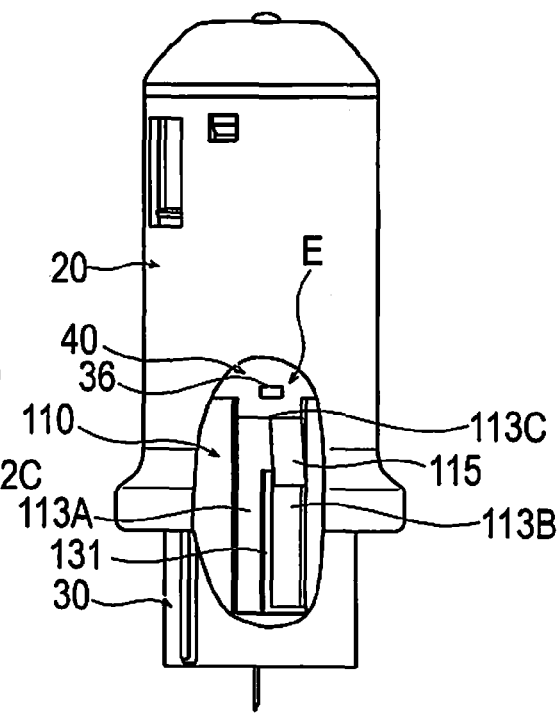
Fig. 28
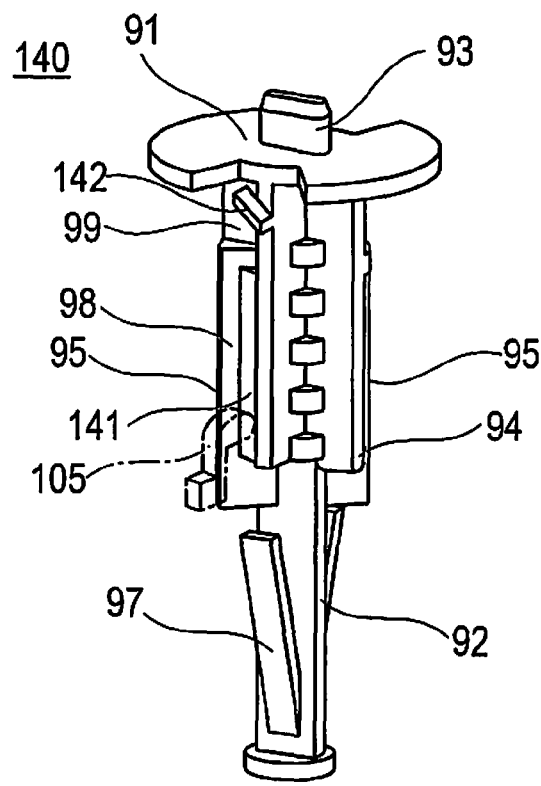

LIQUID ADMINISTRATION DEVICE

CROSS-REFERENCE TO RELATED APPLICATIONS

This application claims priority to Japanese Patent Application No. 2014-047697, filed on Mar. 11, 2014 which is hereby incorporated by reference in its entirety.

BACKGROUND

Technical Field

The present disclosure relates to a liquid administration device for administering a liquid into a living body.

Background Art

In the related art, a prefilled syringe, which is previously filled with a liquid such as a medicine, is known. In general, the prefilled syringe includes a syringe outer cylinder in which a liquid is accommodated and that is formed with a discharge port at a distal end through which the liquid is discharged, a needle tube that is provided in the discharge port of the syringe outer cylinder, a gasket that is slidable in the syringe outer cylinder, and a plunger for pressing the gasket in a distal direction.

The prefilled syringe is also used when a patient performs self administration at home. For this reason, a configuration has been proposed (for example, refer to US2011/0092915A) in which a needle tube is covered with a cover member that is biased by a spring, in order to improve safety. Such a prefilled syringe has a configuration in which, when performing administration, the skin is punctured with a needle tube protruding by pressing the cover member to the skin of an object of administration, and after the administration, the cover member is separated from the skin of the object of administration in order to cover the needle tube by advancing the cover member using the spring. With such a configuration, the needle tube is covered with the cover member except when puncturing, and therefore, erroneous puncturing is suppressed and safety is enhanced.

Since the cover member is also biased by the spring during the administration, there is a concern that, if pressing force is erroneously weakened in the middle of the administration, the cover member is moved by the spring so as to cover the needle tube which is then pulled out from a living body, and thus, it is difficult to perform administration.

In addition, in a case where an exposure restriction unit that restricts the movement of the cover member so as not to expose the needle tube again is provided in the prefilled syringe, when the cover member moves so as to cover the needle tube after the administration, if the pressing is erroneously weakened in the middle of the administration, the exposure restriction unit is operated to cover the needle tube with the cover member, and therefore, it is impossible to continue the administration regardless of being in the middle of the administration.

SUMMARY OF INVENTION

In light of the foregoing, one objective of certain embodiments of the present invention is to provide a liquid administration device with which it is possible to improve operability while securing safety by providing a cover member that covers a needle tube in a manner in which the needle tube can be exposed and allows administration to resume even if the administration operation is suspended in the middle of the administration.

According to one embodiment, a liquid administration device is used for administering a liquid into a living body, and includes an operation unit for performing operation by being gripped, a structure that includes an accommodation body capable of accommodating the liquid therein and a needle tube communicatable with the inside of the accommodation body and that is relatively rotatable with respect to the operation unit and movable in an axial direction of the rotation, a cover member that is movable between a protection position at which the needle tube is covered and an exposure position from which the needle tube is exposed, a biasing member that biases the cover member in the distal direction, an exposure restriction unit that restricts movement of the cover member to the exposure position when the movement amount of the cover member, which moves from the exposure position to the protection position using biasing force of the biasing member, with respect to the structure reaches a predetermined exposure restriction operation amount, and a movement amount restriction unit that restricts the movement amount of the cover member such that the movement amount of the cover member with respect to the structure does not reach the exposure restriction operation amount due to the biasing force of the biasing member until the movement amount of the operation unit with respect to the structure in the distal direction reaches a predetermined movement amount for completion of the administration.

In the liquid administration device that is configured as described above, safety can be secured by providing a cover member that covers a needle tube in a manner in which the needle tube can be exposed, and interruption of operation due to movement of the cover member during administration can be suppressed by a movement amount restriction unit restricting the movement amount of the cover member Therefore, operability can be improved. Furthermore, with the provision of the movement amount restriction unit, the movement amount of the cover member with respect to the structure does not reach an exposure restriction operation amount until the movement amount of the operation unit with respect to the structure in the distal direction reaches a movement amount for completion of the administration. Therefore, the movement of the cover member to the exposure position is not restricted until the administration is completed and the movement amount of the cover member with respect to the structure reaches the exposure restriction operation amount, and it is possible to resume administration even if the administration operation is suspended in the middle of the administration.

BRIEF DESCRIPTION OF DRAWINGS

FIG. 10(A) is a perspective view having a cam groove as a center and FIG. 10(B) is a perspective view having a safety groove as a center.

FIG. 12(A) shows an operation guide portion and FIG. 12(B) shows an exposure restriction unit.

FIG. 13(A) shows the operation guide portion and FIG. 13(B) shows the exposure restriction unit.

FIG. 16(A) shows the operation guide portion and FIG. 16(B) shows the exposure restriction unit.

FIG. 19(A) shows the operation guide portion and FIG. 19(B) shows the exposure restriction unit.

FIG. 20(A) shows the operation guide portion and FIG. 20(B) shows the exposure restriction unit.

FIG. 21 is a cross-sectional view showing a state in which administration of the liquid using the liquid administration device according to the embodiment is completed.

FIGS. 22(A) and 22(B) are side surface views illustrating the liquid administration device according to the embodiment in an operation state when the operation unit reaches a movement amount for the completion of the administration of the liquid. FIG. 22(A) shows the operation guide portion and FIG. 22(B) shows the exposure restriction unit.

FIGS. 23(A) and 23(B) are side surface views illustrating the liquid administration device according to the embodiment in an operation state when the administration of the liquid is complete and the cover is separated from the object. FIG. 23(A) shows the operation guide portion and FIG. 23(B) shows the exposure restriction unit.

FIG. 25(A) shows an operation guide portion and FIG. 25(B) shows an exposure restriction unit.

FIG. 26(A) shows an operation guide portion and FIG. 26(B) shows an exposure restriction unit.

FIGS. 27(A) and 27(B) are side surface views illustrating an operation state of another modification example of the liquid administration device according to the embodiment where a holding portion for suspension is formed parallel a linear grove. FIG. 27(A) shows an operation guide portion and FIG. 27(B) shows an exposure restriction unit.

FIG. 28 is a perspective view showing a plunger of still another modification example of the liquid administration device according to the embodiment.

FIG. 31(A) shows a state immediately before completion of administration and FIG. 31(B) shows a state at the time of the completion of the administration.

DETAILED DESCRIPTION

Figure 1:
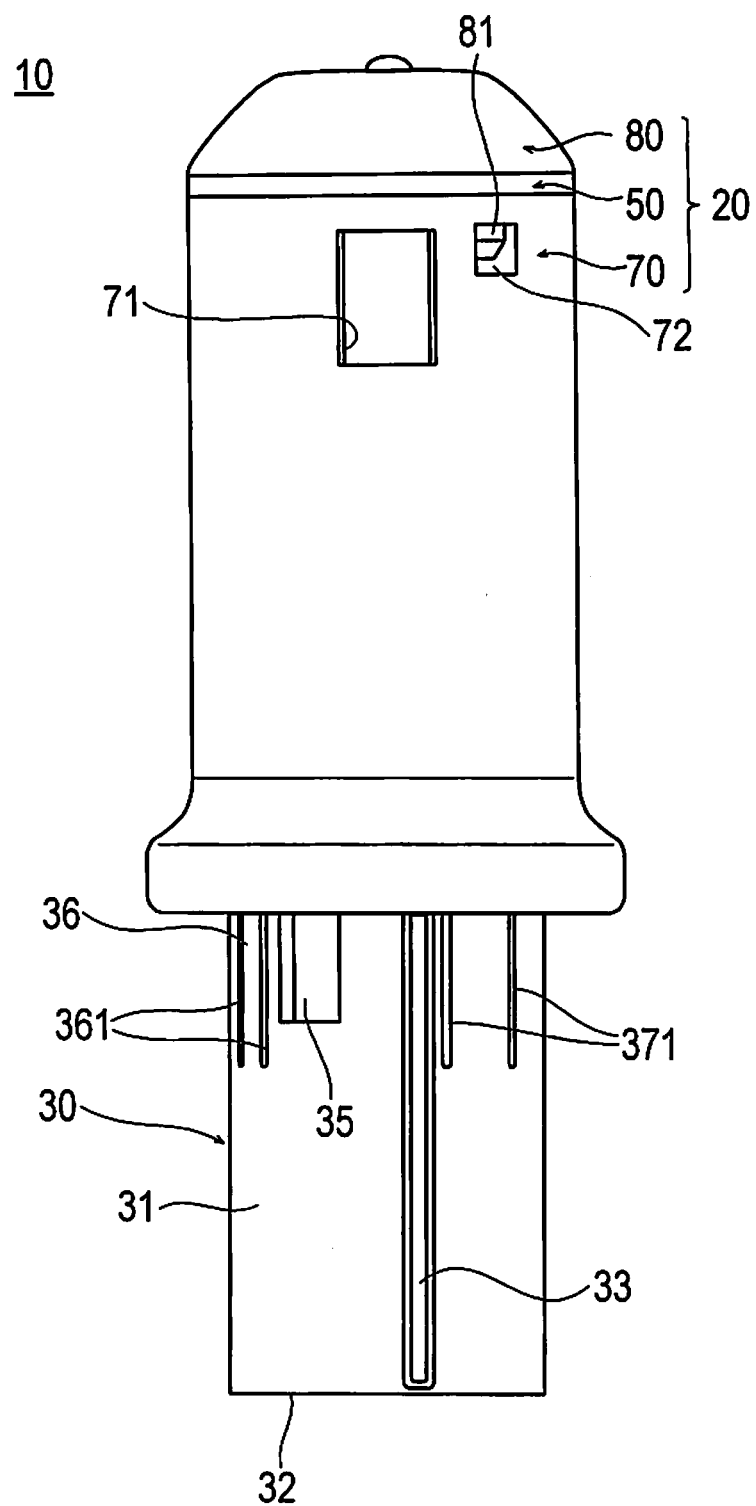
FIG. 1 is a side surface view showing a liquid administration device according to an embodiment.

Hereinafter, embodiments of the present invention will be described with reference to accompanying drawings. Note that, in some cases, dimensional ratios in the drawings are exaggerated and are different from the actual ratios for the convenience of description. In addition, in the description below, the operation side (side on which a user presses) of a liquid administration device will be referred to as a "proximal side", and the side from which a needle tube protrudes and through which a liquid is administered will be referred to as a "distal side".

Figure 2:
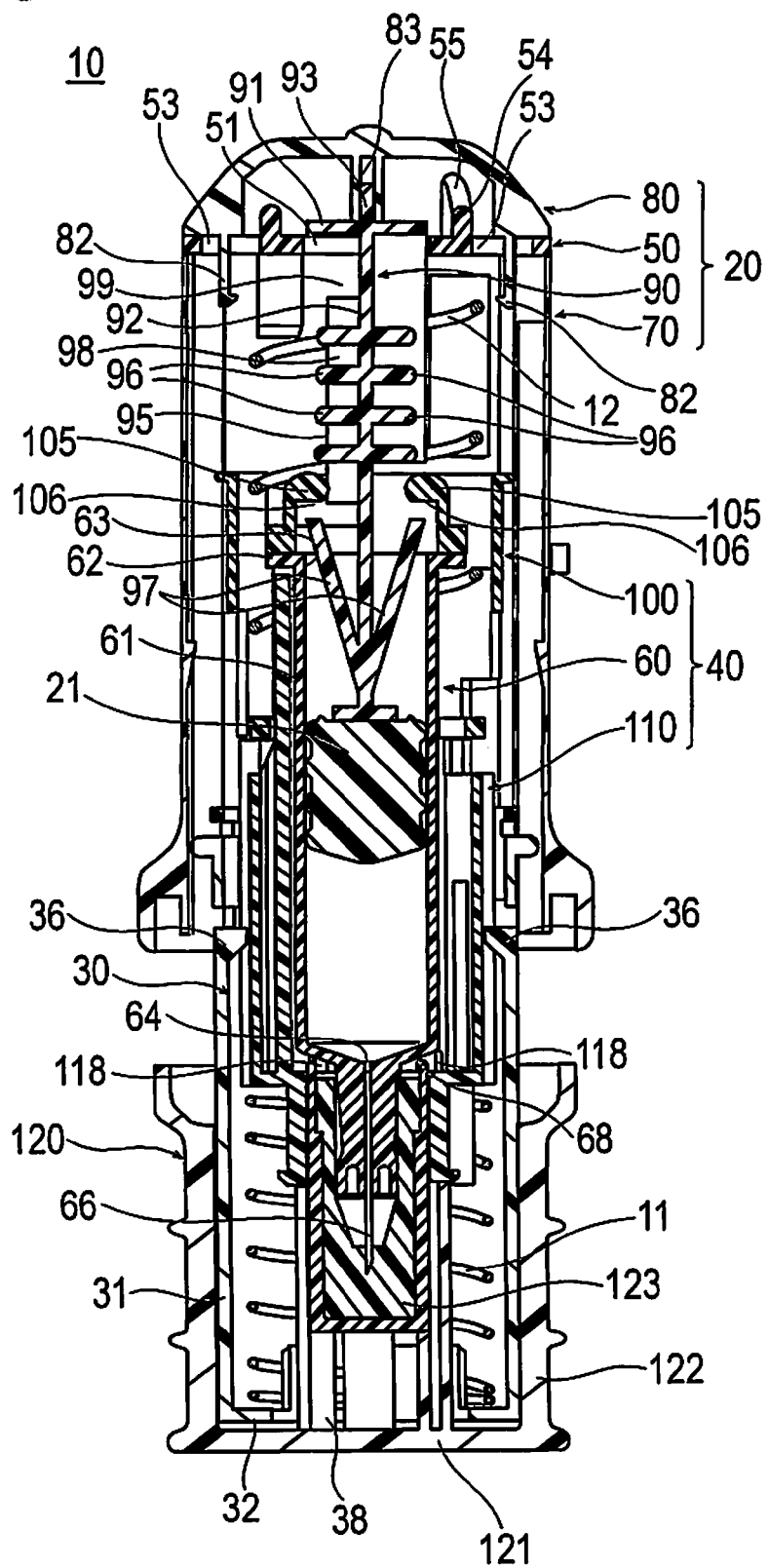
FIG. 2 is a longitudinal cross-sectional view showing the liquid administration device according to the embodiment.
Figure 3:
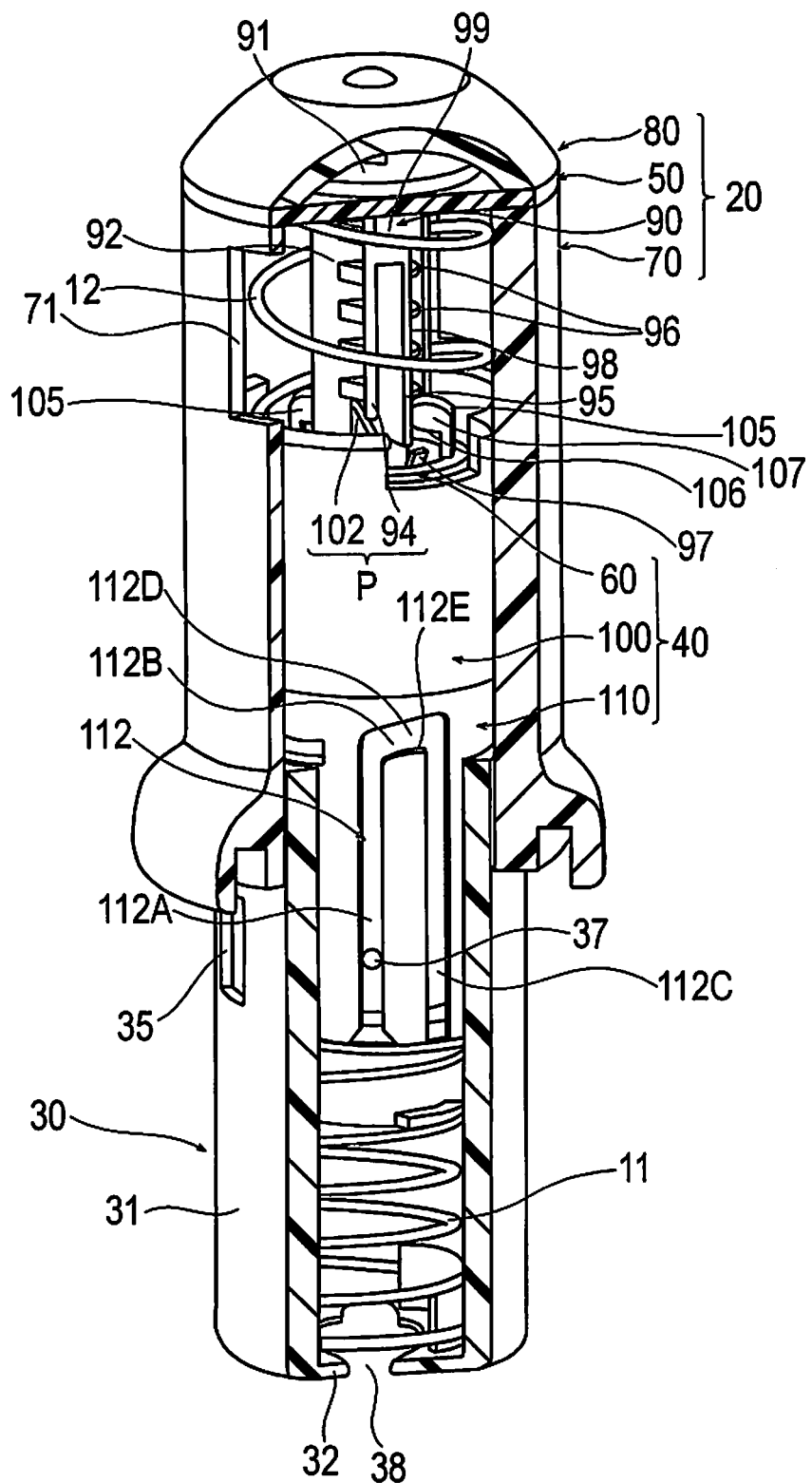
FIG. 3 is a perspective cross-sectional view that is partially cut and shows the liquid administration device according to the embodiment.
Figure 4:
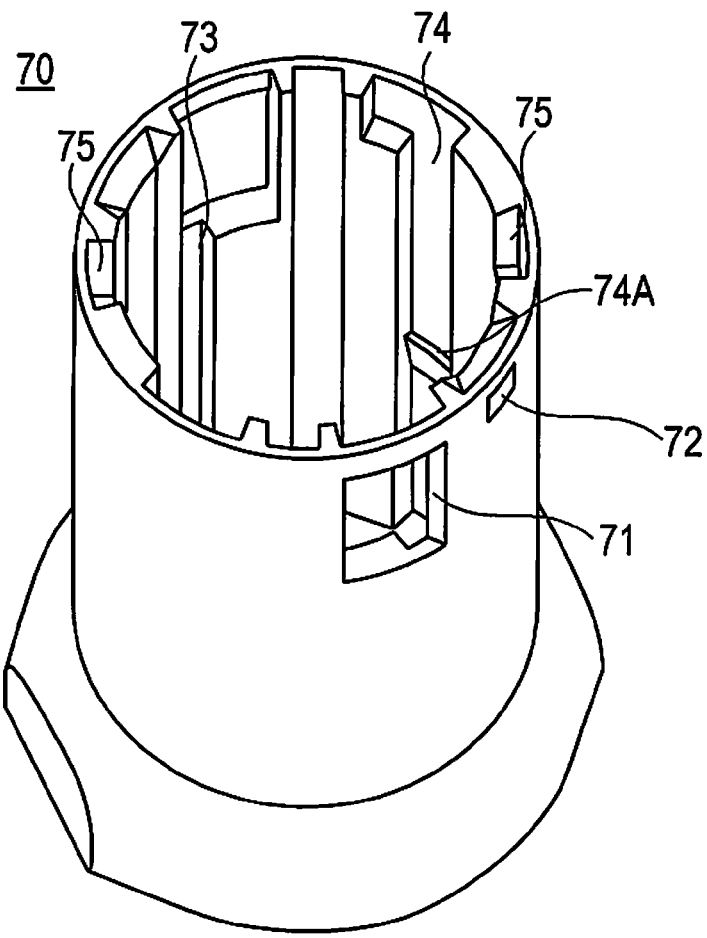
FIG. 4 is a perspective view showing an operation unit cylinder.
Figure 5:
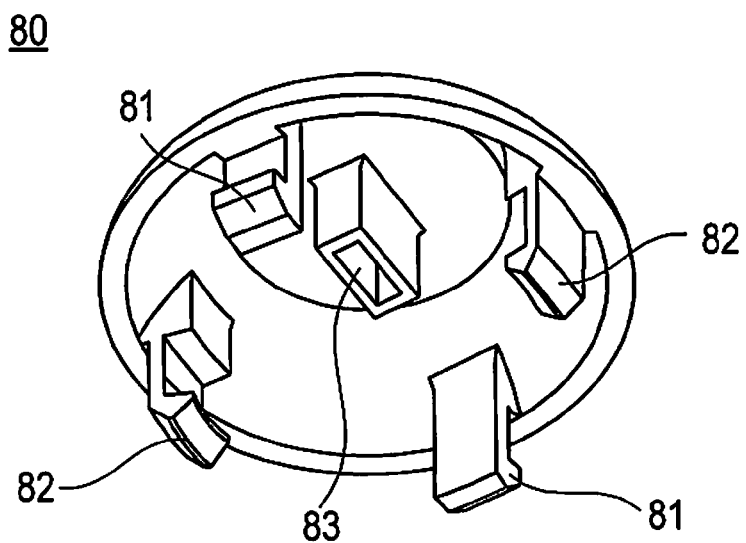
FIG. 5 is a perspective view showing an operation unit proximal member.
Figure 6:
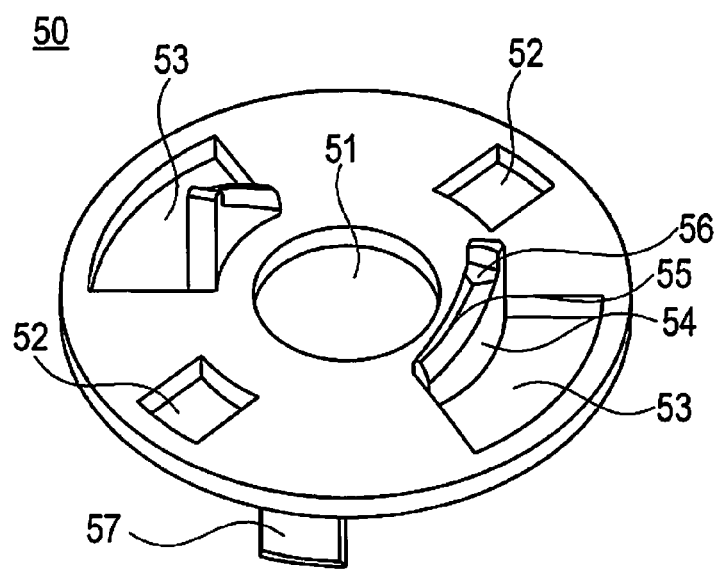
FIG. 6 is a perspective view showing an engagement plate.

A liquid administration device 10 according to an embodiment shown in FIGS. 1 to 3 is a medical device for administering a liquid such as a medicine into a living body.

The liquid administration device 10 includes an operation unit 20 (upper housing) that is gripped and operated by a user, a cover member 30 that is provided so as to be movable to the operation unit 20, a structure 40 that is provided so as to be rotatable inside the operation unit 20 and the cover member 30, a second coil spring 11 (biasing member) that biases the cover member 30 to the structure 40 in the distal direction, and a first coil spring 12 (biasing member) that is disposed inside the operation unit 20.

In general, the liquid administration device 10 is provided in a state in which the cover member 30 and a needle tube 66 are covered with a cap 120, which is then removed for use.

The operation unit 20 is a part that a user grips and at which administration of a liquid is operated. The operation unit includes a cylindrical operation unit cylinder 70 that a user grips and presses, an operation unit proximal member 80 that is provided so as to close an opening of a proximal side of the operation unit cylinder 70, a plunger 90, an engagement plate 50 that is interposed between the operation unit cylinder 70 and the operation unit proximal member 80 and is engaged with the first coil spring 12, and a gasket 21 that is pressed and moved by the plunger 90.

As shown in FIGS. 1 to 4, the operation unit cylinder 70 is disposed so as to surround an outer peripheral surface of the structure 40 and is formed with a first window portion 71, through which it is possible to observe the inside from the outside, and two operation unit engagement holes 72 for engaging the operation unit proximal member 80. In addition, two operation unit first grooves 73 and two operation unit second grooves 74 that extend in an axial direction and two positioning concave portions 75 are formed on an inner peripheral surface of the operation unit cylinder 70.

The first window portion 71 is formed in a through-hole penetrating from the outer peripheral surface to the inner peripheral surface. In addition, the first window portion may be formed of a transparent material. The structure 40 and the cover member 30 that are disposed inside the operation unit cylinder 70 can be observed through the first window portion 71. It is possible to grasp the progress of administration by members observed through the first window portion 71.

Two operation unit engagement holes 72 are provided at positions opposite to each other across a central axis of the operation unit 20 and are formed in through-holes penetrating from the outer peripheral surface to the inner peripheral surface. Note that the operation unit engagement holes 72 may not be the through-holes as long as the operation unit proximal member 80 can be engaged therewith.

Figure 8:
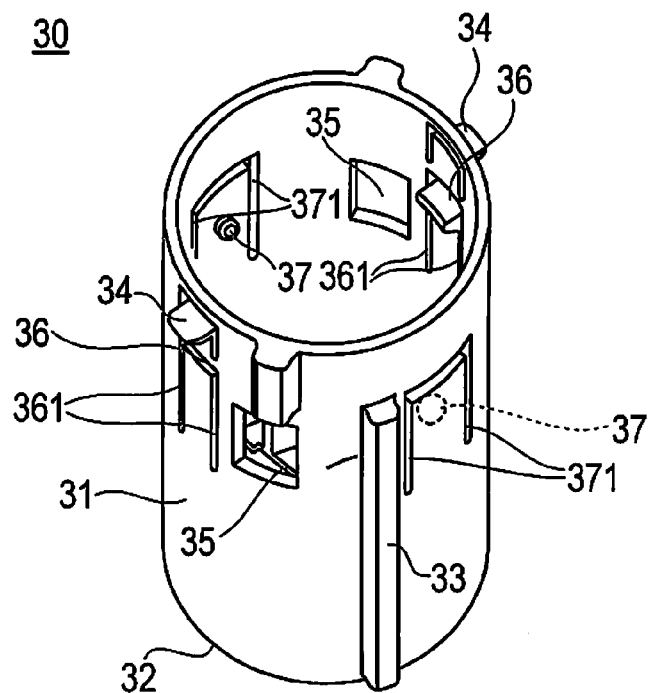
FIG. 8 is a perspective view showing a cover member.

The two operation unit first grooves 73 are provided at positions opposite to each other across the central axis of the operation unit 20 and each accommodates a guiding rib 33 (refer to FIG. 8) formed on an outer peripheral surface of the cover member 30 to be described later so as to be movable in an axial direction. The two operation unit second grooves 74 are provided at positions opposite to each other across the central axis of the operation unit and each accommodates a separation prevention convex portion 34 (refer to FIG. 8) that is formed on the outer peripheral surface of the cover member 30 to be described later so as to be movable in the axial direction. A pullout prevention rib 74A for preventing the cover member 30 from being pulled out is formed in the middle of the operation unit second groove 74.

As shown in FIGS. 1 to 3 and 5, the operation unit proximal member 80 includes two operation unit engagement claws 81 that are engaged with the operation unit cylinder 70, two noise generation claws 82 (noise generation portions) for generating noise by being engaged with a rotary cylinder proximal portion 100, and a plunger interlock hole 83 for interlocking the plunger 90.

The two operation unit engagement claws 81 are provided at positions opposite to each other across the central axis of the operation unit 20 therebetween and can be engaged with the operation unit engagement holes 72 of the operation unit cylinder 70. With the engagement of the operation unit engagement claw 81 with the operation unit engagement hole 72, the operation unit cylinder 70 along with the operation unit proximal member 80 and the plunger 90 along with the engagement plate 50 that are interposed therebetween are constituted so as to be integrally moved.

The plunger interlock hole 83 is formed in a central portion of the operation unit proximal member 80, and a part of the plunger 90 on the proximal side can be inserted therein.

As shown in FIGS. 1 to 3 and 6, the engagement plate 50 is a disc-shaped member disposed so as to be interposed between the operation unit cylinder 70 and the operation unit proximal member 80. The engagement plate 50 is formed with a plunger insertion hole 51 through which the plunger 90 is inserted, two noise generation insertion holes 52 through which the noise generation claws 82 are penetrated, two engagement claw insertion holes 53 through which the operation unit engagement claws 81 are penetrated, and two positioning convex portions 57. A spring engagement portion 54 that protrudes toward the proximal side and with which the first coil spring 12 is engaged is formed at an inner edge of the engagement claw insertion hole 53 on the proximal side.

The two noise generation insertion holes 52 are provided at positions opposite to each other across a central axis of the engagement plate 50. The two engagement claw insertion holes 53 are provided at positions opposite to each other across the central axis of the engagement plate 50 therebetween.

Figure 14:
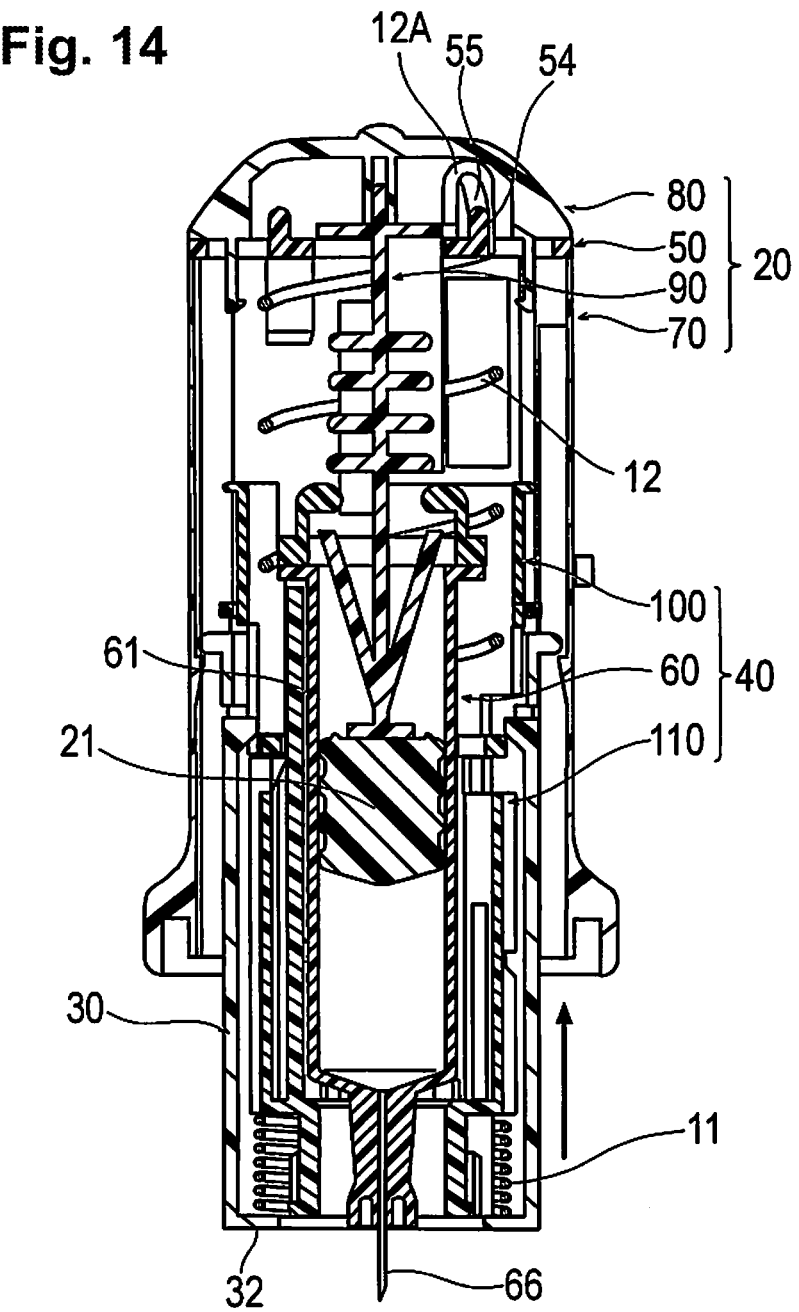
FIG. 14 is a cross-sectional view showing a state in which the cover member of the liquid administration device according to the embodiment is moved and an object is punctured with a needle tube.

The spring engagement portion 54 is formed within a predetermined angle range in a circumferential direction, and is formed with a spring movement slope 55 of which the protruding height of the spring engagement portion in the proximal direction inclines in the circumferential direction. The spring movement slope 55 is a part, with which a spring proximal portion 12A (refer to FIG. 14) of the first coil spring 12 formed in a hook shape, is engaged (caught) so as to be movable along the slope. A flat spring engagement surface 56 on which the spring proximal portion 12A of the first coil spring 12 is caught in an initial state before operation is formed on the top of the spring movement slope 55.

The two positioning convex portions 57 are provided at positions opposite to each other across the central axis of the engagement plate 50, and the engagement plate 50 can be interlocked with the operation unit cylinder 70 at a precise position by the positioning convex portions being fitted into the positioning concave portions 75 of the operation unit cylinder 70.

Figure 7:
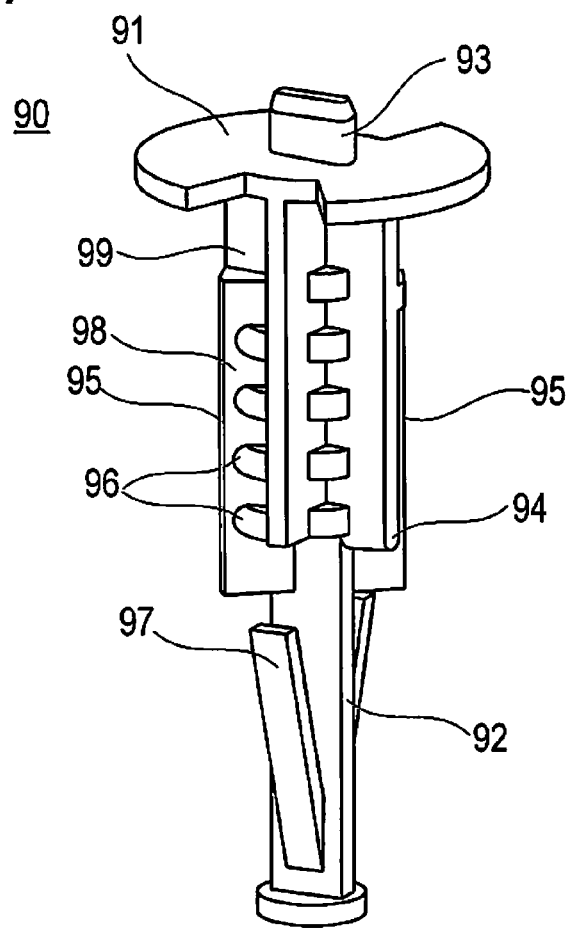
FIG. 7 is a perspective view showing a plunger.

As shown in FIGS. 2, 3, and 7, the plunger 90 is disposed so as to be interposed between the engagement plate 50 and the operation unit proximal member 80. The plunger 90 includes a plunger flat plate portion 91 that has a flat shape and is interposed between the engagement plate 50 and the operation unit proximal member 80, and a plunger main body portion 92 that extends from a central portion of the plunger flat plate portion 91 in the distal direction.

A plunger interlocking convex portion 93 that extends from the central portion in the proximal direction is formed on the plunger flat plate portion 91. The plunger interlocking convex portion 93 is inserted into a plunger interlock hole 83 of the operation unit proximal member 80 to interlock the plunger 90 with the operation unit proximal member 80.

The plunger main body portion 92 is a part that presses the gasket 21 provided in a syringe 60 for discharging a liquid accommodated in the syringe 60. The plunger main body portion 92 includes two plunger locking projection portions 94 that restrict movement of the plunger 90 with respect to a syringe cylinder 61 until a predetermined condition is satisfied, two movement amount restriction units 95 that restrict rotation of the structure 40 with respect to the operation unit 20 until a predetermined condition is satisfied, a plurality of resistance projection portions 96 arranged in a direction along the central axis of the plunger 90, and two movement prevention claw portions 97 that prevent the structure 40 from being moved to the distal side of the operation unit 20.

The two plunger locking projection portions 94 are parts that are provided at positions opposite to each other across the central axis of the plunger 90 and can come into contact with a plunger locking inclined portion 102 (refer to FIGS. 3 and 9) of the rotary cylinder proximal portion 100 to be described later. With disposition of the plunger locking inclined portion 102 on the distal side, the plunger locking projection portions 94 restrict movement of the plunger locking inclined portion 102 in the proximal direction to restrict discharge of a liquid accommodated in the syringe 60 due to the gasket 21 moving within the syringe 60. When the plunger locking inclined portion 102 is rotated to move from the distal side of the plunger locking projection portion 94, the plunger locking inclined portion 102 can be moved in the proximal direction, and therefore, the liquid accommodated in the syringe 60 can be discharged due to the gasket 21 moving within the syringe 60 (refer to FIG. 15). That is, the plunger locking projection portion 94 and the plunger locking inclined portion 102 function as a plunger restriction unit P that restricts the movement of the plunger 90 until a predetermined condition is satisfied and restricts the discharge of the liquid from the syringe 60.

The two movement amount restriction units 95 are provided at positions opposite to each other across the central axis of the plunger 90 and are formed to have a predetermined length from the proximal end to the distal end. The two movement amount restriction units 95 are formed with a sliding surface 98 on which an attachment portion 107 (refer to FIGS. 3 and 9) of the rotary cylinder proximal portion 100 to be described later is pressed by rotation of the rotary cylinder proximal portion 100 to be described later. The sliding surface 98 holds the attachment portion 107 so as to be slidable in a state where the attachment portion 107 is pressed. An accommodation portion 99 that receives the attachment portion 107 by allowing the rotation of the attachment portion so as to release the rotation restriction of the attachment portion 107 that has been moved in the proximal end by sliding on the sliding surface 98 is formed on the proximal side of the movement amount restriction unit 95. Accordingly, the movement amount restriction unit 95 restricts the relative rotation of the structure 40 and the operation unit 20 until the administration of a liquid is completed and the movement amount of the operation unit 20 with respect to the structure 40 reaches a movement amount for the completion of the administration, and the attachment portion 107 is received by the accommodation portion 99. Note that the movement amount means a relative change amount of the position of the structure, and specifically means a change amount of relative positions of the cover member 30 and the structure 40 or a change amount of relative positions of the operation unit 20 and the structure 40, for example. The movement amount (change amount) is not limited to be represented only by the relative movement distance and includes at least one of the relative movement distance and the relative rotary angle.

The plurality of resistance projection portions 96 are arranged at positions opposite to each other across the central axis of the plunger 90, laterally protrude, and connect between the plunger locking projection portion 94 and the movement amount restriction unit 95. Four resistance projection portions 96 are symmetrically arranged at positions opposite to each other across the central axis in a direction along the central axis of the plunger 90, and the protruding height is set to be lower toward the proximal side of the resistance projection portions 96. Note that the number of the resistance projection portions 96 is not particularly limited.

The two movement prevention claw portions 97 are provided at positions opposite to each other across the central axis of the plunger 90 and laterally extends while inclining in the proximal direction. The movement prevention claw portions 97 are accommodated in the syringe 60 and can come into contact with a distal end surface 106 (refer to FIGS. 3 and 9) of resistance claw portions 105 of the rotary cylinder proximal portion 100 to be described later.

As shown in FIGS. 1 to 3 and 8, the cover member 30 includes a cylindrical cover cylinder 31 and a planar cover distal portion 32 that is formed so as to close an opening of the cover cylinder 31 on the distal side. The cover member 30 is biased to the structure 40 in the distal direction due to a biasing force of the second coil spring 11, and therefore, it is possible to move the needle tube 66 between a protection position and an exposure position from which the needle tube 66 is exposed.

Two second window portions 35 are formed in the cover cylinder 31 in order to observe the inside of the syringe 60 from the outside. The two second window portions 35 are provided at positions opposite to each other across the central axis of the cover cylinder 31 and are formed in through-holes penetrating from the outer peripheral surface to the inner peripheral surface of the cover cylinder 31. Note that the second window portions 35 may be formed transparent material instead of the through-holes.

Two guiding ribs 33 extending in the axial direction and two separation prevention convex portions 34 are formed on the outer peripheral surface of the cover cylinder 31. The two guiding ribs 33 are provided at positions opposite to each other across the central axis of the cover member 30 so as to protrude radially outward from the cover member and are accommodated in the operation unit first grooves 73 (refer to FIG. 4) of the operation unit 20. Accordingly, the cover member 30 can relatively move only in the axial direction without being relatively rotated with respect to the operation unit 20. In addition, it is possible to suppress rattling of the cover member 30 against the operation unit 20 using the guiding rib 33 engaged with the operation unit first groove 73.

The two separation prevention convex portions 34 are provided at positions opposite to each other across the central axis of the cover member 30 so as to protrude radially outward from the cover member and are accommodated in operation unit second grooves 74 of the operation unit 20. The separation prevention convex portion 34 prevents the cover member 30 from being completely separated from the operation unit 20 since the separation prevention convex portion 34 is caught in the pullout prevention rib 74A (refer to FIG. 4) of the operation unit second groove 74 when the operation unit 20 and the cover member 30 are relatively separated along the axial direction.

Two safety convex portions 36 (first engagement portions) and two guiding convex portions 37 are formed on the inner peripheral surface of the cover cylinder 31. The two safety convex portions 36 are provided at positions opposite to each other across the central axis of the cover member 30 so as to protrude radially inward from the cover member and are accommodated in safety grooves 113 (refer to FIGS. 10(A) and 10(B)) of the structure 40 to be described later. Each safety convex portion 36 is interposed between slits 361 formed in the cover cylinder 31, and therefore, is movable so as to be bent radially outward of the cover cylinder.

The two guiding convex portions 37 are provided at positions opposite to each other across the central axis of the cover member 30 so as to protrude radially inward from the cover member, and are accommodated in a cam groove 112 (refer to FIGS. 10(A) and 10(B)) of the structure 40 to be described later. Each guiding convex portion 37 is interposed between the slits 371 formed in the cover cylinder 31, and therefore, is movable so as to be bent radially outward of the cover cylinder.

An opening portion 38 through which the needle tube 66 is passed in the distal direction is formed on the central axis of the cover member 30 in the cover distal portion 32 of the cover member 30.

As shown in FIGS. 2 and 3, the structure 40 is provided inside the operation unit 20 and the cover member 30 so as to be relatively movable with respect to the operation unit 20 and the cover member 30. The structure 40 includes the syringe 60, the rotary cylinder proximal portion 100 (intermediate housing) provided on the proximal side, and the rotary cylinder distal portion 110 (lower housing) interlocked on the distal side of the rotary cylinder proximal portion 100. The rotary cylinder proximal portion 100 and the rotary cylinder distal portion 110 are rotatable around the central axis of the operation unit 20 and the cover member 30.

As shown in FIG. 2, the syringe 60 includes the cylindrical syringe cylinder 61 capable of accommodating a liquid therein. The needle tube 66 is attached to the distal end of the syringe cylinder 61.

A proximal end opening portion 63 is formed on a flange 62 on a proximal side of the syringe cylinder 61, and a discharge port 64 through which a liquid is passed is formed on the distal side of the syringe cylinder. The needle tube 66 is fixed to the distal end of the syringe cylinder 61 such that the flow path inside the syringe communicates with the discharge port 64 of the syringe 60, and a sharp needle tip is formed at the distal end. The gasket 21 comes into contact with the distal portion of the plunger main body portion 92, and is disposed so as to be slidable along the axial direction of the syringe cylinder 61 while maintaining liquid-tightness by being brought into close contact with an inner wall surface 65 of the syringe cylinder 61. The liquid in the space defined by the syringe cylinder 61 and the gasket 21 can be discharged from the needle tube 66 through the discharge port 64 by moving the inside of the syringe cylinder 61 in the distal direction using the gasket 21 being pressed by the plunger main body portion 92. Although there is space between the plunger main body portion 92 and the gasket 21 that are interlocked only by contact therebetween, the gasket 21 is hardly rotated with respect to the plunger 90 due to frictional force acting thereon. Note that the gasket 21 and the plunger 90 may be strongly interlocked with each other such that the gasket 21 is not rotatable with respect to the plunger 90. As the interlocking method, for example, attaching them together or interlocking one with another by providing a convex portion in the distal portion of the plunger 90 and providing a concave portion, into which the convex portion is fitted, in the gasket 21 may be employed.

Figure 9:
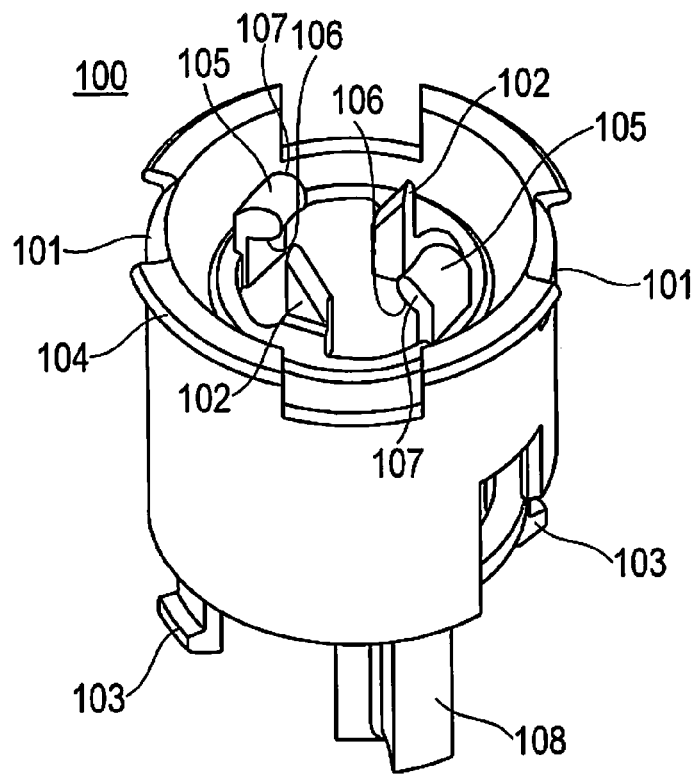
FIG. 9 is a perspective view showing a rotary cylinder proximal portion.

As shown in FIGS. 2, 3, and 9, the rotary cylinder proximal portion 100 includes two noise generation holes 101 with which the noise generation claws 82 (refer to FIG. 5) are engaged, two plunger locking inclined portions 102 coming into contact with the plunger locking projection portions 94, two rotary cylinder engagement claws 103 engaged with the rotary cylinder distal portions 110, resistance claw portions 105 coming into contact with the resistance projection portions 96, and a spring engagement portion 108 with which a spring distal portion of the first coil spring 12 formed in a hook shape is engaged (caught).

The two noise generation holes 101 are formed at positions opposite to each other across a central axis of the structure 40 and generate noise by being engaged with the noise generation claws 82 formed on the operation unit proximal member 80. The two plunger locking inclined portions 102 are formed at positions opposite to each other across the central axis of the structure 40, and as shown in FIG. 3, the two plunger locking inclined portions are positioned on the distal side of the plunger locking projection portions 94 formed in the plunger 90 in an initial state of the provision of the liquid administration device 10 and restrict the movement of the plunger 90 in the distal direction to restrict the administration of a liquid. When the rotary cylinder proximal portion 100 is rotated with respect to the plunger 90 from this state, the plunger locking inclined portion 102 is deviated from the position of the plunger locking projection portion 94 in the distal direction, and the restriction of the movement of the plunger 90 in the distal direction is released, thereby enabling the administration of a liquid. That is, the plunger locking inclined portion 102 and the plunger locking projection portion 94 function as a plunger restriction unit P that restricts the movement of the plunger 90 until a predetermined condition is satisfied.

Figure 10A:
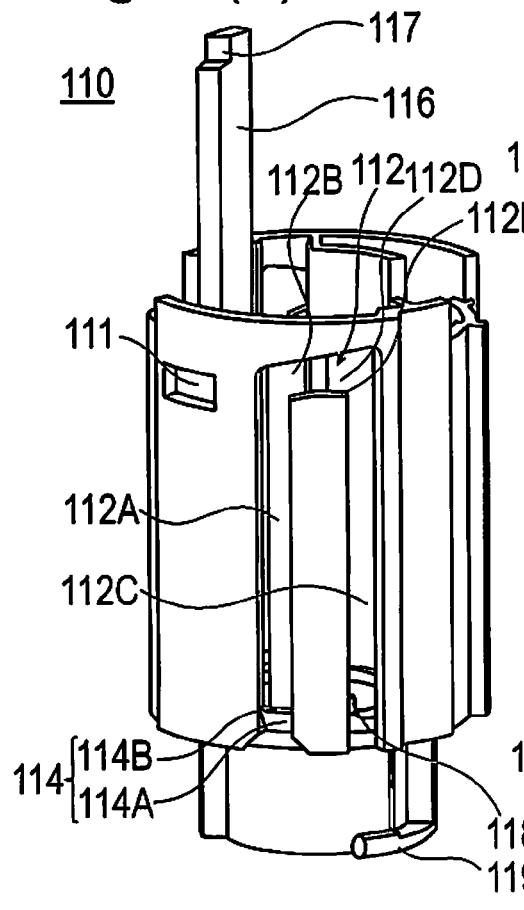
FIGS. 10(A) and 10(B) are views showing a rotary cylinder distal portion.
Figure 10B:
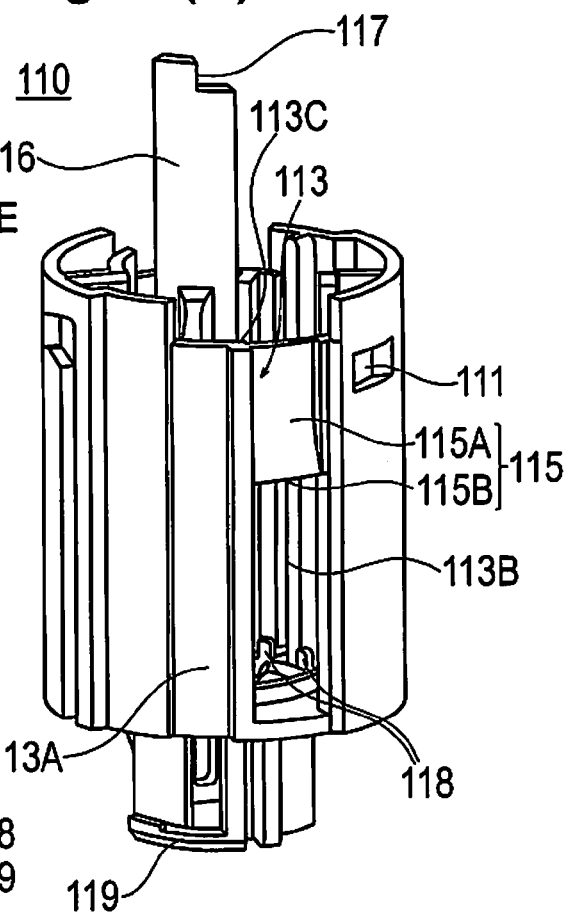
Figure 11:
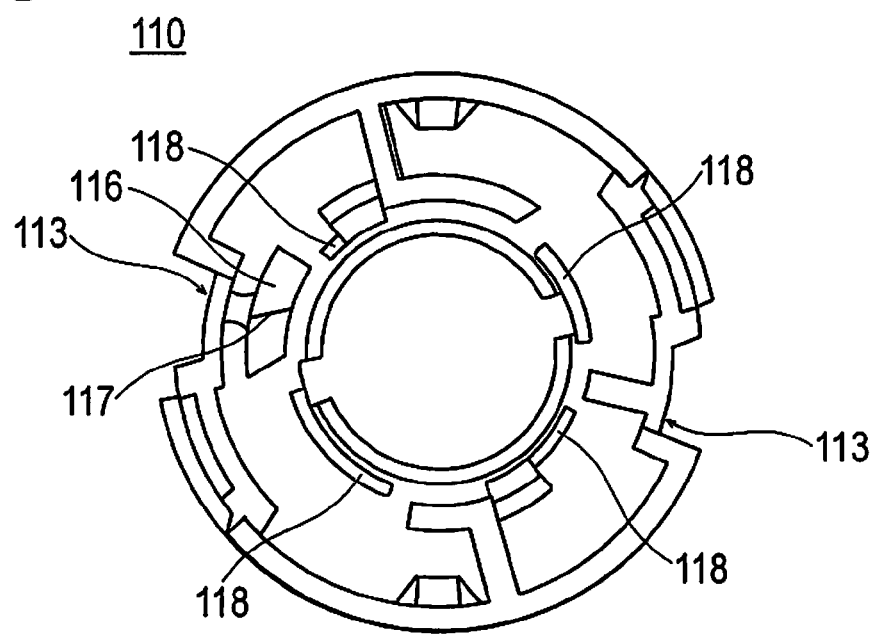
FIG. 11 is a plan view showing the rotary cylinder distal portion.

The two rotary cylinder engagement claws 103 are formed at positions opposite to each other across the central axis of the structure 40 and are engaged with rotary cylinder engagement holes 111 (refer to FIGS. 10(A) and 10(B)) formed in the rotary cylinder distal portions 110. The rotary cylinder proximal portion 100 and the rotary cylinder distal portions 110 are constituted so as to be integrally moved by the rotary cylinder engagement claws 103 being engaged with the rotary cylinder engagement holes 111.

The proximal portion of the outer peripheral surface of the rotary cylinder proximal portion 100 is formed with a flange-shaped outer peripheral convex portion 104 protruding radially outward of the rotary cylinder proximal portion.

The two resistance claw portions 105 are formed at positions opposite to each other across the central axis of the structure 40 and protrude radially inward from the rotary cylinder proximal portion. The two resistance claw portions 105 apply resistance force by being sequentially brought into contact with the plurality of resistance projection portions 96 when the operation unit 20 moves to the rotary cylinder proximal portion 100 in the distal direction. The movement prevention claw portion 97 provided in the operation unit 20 can come into contact with the distal end surface 106 formed on the distal side of the resistance claw portion 105 when the operation unit 20 is moved to the rotary cylinder proximal portion 100 in the proximal direction (refer to FIG. 2).

In addition, the attachment portion 107 that is a surface that restricts rotation of the rotary cylinder proximal portion 100 with respect to the operation unit 20 by being brought into contact with the sliding surface 98 is formed on the resistance claw portion 105.

As shown in FIGS. 2, 3, 10(A), 10(B), and 11, the two rotary cylinder engagement holes 111 with which the rotary cylinder engagement claws 103 (refer to FIG. 9) of the rotary cylinder proximal portion 100 are engaged, two cam grooves 112, and two safety grooves 113 are formed on the outer peripheral surface of the rotary cylinder distal portion 110.

The two rotary cylinder engagement holes 111 are formed at positions opposite to each other across the central axis of the structure 40, and the rotary cylinder engagement claws 103 formed in the rotary cylinder proximal portion 100 are engaged with the rotary cylinder engagement holes.

The two cam grooves 112 are formed at positions opposite to each other across the central axis of the structure 40, accommodate the guiding convex portions 37 (refer to FIG. 8) of the cover member 30, and relatively move the guiding convex portions 37 along the groove. That is, the cam groove 112 and the guiding convex portion 37 function as an operation guide portion M that is constituted of a cam mechanism defining relative movement of the structure 40 and the cover member 30.

The cam groove 112 includes an initial linear groove 112A that extends along the axial direction of the rotary cylinder distal portion 110 and is formed in a linear shape, an inclined groove 112B that is formed so as to be inclined in the axial direction of the rotary cylinder distal portion 110, and a linear groove 112C that extends along the axial direction of the rotary cylinder distal portion 110 and is formed in a linear shape.

The initial linear groove 112A is formed so as to extend from the distal portion of the outer peripheral surface in the proximal direction. A stepped portion 114 that receives the guiding convex portion 37 so as to be undetachable to the initial linear groove 112A is formed in the distal portion of the initial linear groove 112A when assembling the device. The stepped portion 114 can guide the guiding convex portion 37 to the initial linear groove 112A while making the guiding convex portion 37 slip along a slope 114A since the distal side thereof is formed so as to be inclined inside thereof. In addition, the stepped portion 114 is formed with a wall surface 114B that perpendicularly rises at about 90 degrees with respect to the axial direction of the rotary cylinder distal portion 110 on the proximal side and prevents the guiding convex portion 37, which has passed the proximal side of the stepped portion 114 through the slope 114A once, from being separated by passing the wall surface 114B of the stepped portion 114 again.

The inclined groove 112B is formed to communicate with the proximal portion of the initial linear groove 112A and obliquely extends from the proximal portion of the initial linear groove 112A in the proximal direction. The inclined groove 112B is formed to be shorter than one turn.

A holding portion for suspension 112D is provided immediately in front of a part of the inclined groove 112B communicating with the linear groove 112C, and an edge for suspension 112E that is formed at an angle orthogonal to the axial direction of the rotary cylinder distal portion 110 is formed at an edge on the distal side of the holding portion for suspension 112D. The holding portion for suspension 112D is a part by which the guiding convex portion 37 of the cover member 30 is held when suspending the administration. Note that the edge for suspension 112E may not be formed at the angle orthogonal to the axial direction of the rotary cylinder distal portion 110 and may be formed so as to be inclined from the initial linear groove 112A to the linear groove 112C in the distal direction, that is, so as to be inclined in a reversed direction of the inclination angle of the inclined groove 112B.

The linear groove 112C is formed to communicate with the proximal portion of the inclined groove 112B and extends from the proximal portion of the inclined groove 112B in the distal direction.

Note that the cam groove 112 may be formed in the cover member 30 and the guiding convex portion 37 may be formed in the structure 40.

The two safety grooves 113 are formed at positions opposite to each other across the central axis of the structure 40 and accommodate safety convex portions 36 of the cover member 30. The safety groove 113 restricts the relative movement of the cover member 30 with respect to the structure 40 in the axial direction in accordance with the positional relationship between the structure 40 and the cover member 30 that relatively move using the cam groove 112 and the guiding convex portion 37. Accordingly, after the movement amount of the cover member 30 with respect to the structure 40 in the distal direction reaches a predetermined exposure restriction operation amount after the cover member 30 moves to the structure 40 in the proximal direction, that is, a living body is punctured with the needle tube 66 and the administration of a liquid is completed, the safety groove 113 and the safety convex portion 36 constitute an exposure restriction unit E (refer to FIG. 12(B)) that suppresses protruding of the needle tube 66 due to the cover member 30 being moved back to the structure 40 in the proximal direction.

The safety groove 113 includes a first safety groove 113A that extends in the axial direction of the rotary cylinder distal portion 110 and is formed in a linear shape, a second safety groove 113B that extends in parallel to the first safety groove 113A, and a proximal side communication groove 113C in which the first safety groove 113A and the second safety groove 113B are communicated with each other in the proximal portion.

A safety stepped portion 115 (second engagement portion) that allows movement of the safety convex portion 36 in the distal direction but suppresses movement thereof in the proximal direction, is formed in the second safety groove 113B. The safety slope 115A on the proximal side is formed so as to be inclined from the inside of the second safety groove 113B, and therefore, the safety stepped portion 115 can guide the safety convex portion 36 to the distal side while making the safety convex portion 36 slip along the safety slope 115A. In addition, the safety stepped portion 115 is formed with a safety wall surface 115B that perpendicularly rises at about 90 degrees with respect to the axial direction of the rotary cylinder distal portion 110 on the distal side, and thus the safety convex portion 36, which has passed the safety stepped portion 115 in the distal direction through the safety slope 115A once, is engaged with the safety stepped portion 115, thereby suppressing the safety convex portion 36 from passing the safety stepped portion in the proximal direction again.

When the guiding convex portion 37 is positioned in the initial linear groove 112A in the operation guide portion M, the structure 40 and the cover member 30 enter a first state where the safety stepped portion 115 and the safety convex portion 36 are not arranged on an identical axis parallel to a rotary axis. In the first state, the safety convex portion 36 is positioned in the first safety groove 113A, and therefore, there is no case where the safety stepped portion 115 and the safety convex portion 36 are engaged with each other even if the structure 40 and the cover member 30 relatively move in the axial direction. Then, when the guiding convex portion 37 is positioned in the holding portion for suspension 112D, the structure 40 and the cover member 30 enter a second state where the relative rotation of the operation unit 20 and the structure 40 is restricted by bringing the attachment portion 107 into contact with the sliding surface 98. In addition, when the guiding convex portion 37 is positioned in the linear groove 112C, the structure 40 and the cover member 30 enter a third state where the safety stepped portion 115 and the safety convex portion 36 are arranged on an identical axis parallel to the rotary axis. In the third state, the safety convex portion 36 is positioned in the second safety groove 113B and the structure 40 and the cover member 30 relatively move in the axial direction by a predetermined distance (exposure restriction operation amount), and therefore, the safety stepped portion 115 and the safety convex portion 36 can be engaged with each other. Once the safety convex portion 36 moves to the distal side of the safety stepped portion 115, the proximal end of the safety convex portion 36 comes into contact with the safety wall surface 115B, and therefore, the safety convex portion 36 is suppressed from passing the safety stepped portion 115 in the proximal direction.

Note that the safety groove 113 may be formed in the cover member 30 and the safety convex portion 36 may be formed in the structure 40.

In addition, the rotary cylinder distal portion 110 includes a rotary cylinder extension 116 that extends in the proximal direction, a support portion 118 that supports the syringe cylinder 61 so as to be relatively rotatable, and a rotary-cylinder distal projection portion 119 that protrudes radially outward from the distal portion. The proximal portion of the rotary cylinder extension 116 is formed with a rotation restriction unit 117 that comes into contact with the side surface of the flange 62 so as to restrict rotation of the syringe cylinder 61 around the central axis in one direction. The rotation restriction unit 117 plays a role of disposing the syringe cylinder 61 at a position in a proper rotational direction by being brought into contact with the flange 62 during the assembling. Note that the rotation restriction unit 117 allows rotation of the syringe cylinder 61 around the central axis in a reversed direction without restricting the rotation.

The support portion 118 protrudes in the proximal direction so as to slidably come into contact with a distal surface 68 facing in the distal direction of the syringe cylinder 61. The support portion 118 is formed in a ring shape by being divided into a plurality of parts so as to surround the discharge port 64. Note that the support portion 118 may not be divided into a plurality of parts. When the support portion is divided into a plurality of parts, the contact area between the distal surface 68 and the support portion 118 is reduced, and therefore, the syringe cylinder 61 is easily made to be more slidable, which is more preferable. The support portion 118 comes into contact with the distal surface 68 at its protruding top and the contact area therebetween is small, and therefore, it is possible to support the syringe cylinder 61 so as to be slidable in the rotational direction. The protruding top of the support portion 118 may have a shape of which the contact area is reduced. The protruding top of the support portion 118 preferably has a spherical surface shape so that the syringe cylinder 61 becomes more slidable, which is preferable. In a case where the support portion 118 is divided into at least 3 points and has a circular shape when the distal portion is seen from the proximal portion, and the protruding top thereof has a spherical surface shape, the syringe cylinder 61 becomes more slidable, which is more preferable. Note that the surface coming into contact with the support portion 118 may not be the distal surface 68 as long as the surface coming into contact with the support portion 118 faces the distal direction of the syringe cylinder 61.

At least one of the support portion 118 and the distal surface 68 may be subjected to surface treatment. The contact part can made to be slippery and only the structure 40 can be made to be easily rotated by subjecting the support portion 118 or the distal surface 68 to the surface treatment. Examples of the surface treatment include silicone coating.

When frictional force between the gasket 21 and the inside of the syringe cylinder 61 is larger than frictional force between the support portion 118 and the distal surface 68, the syringe cylinder 61 is fixed by the frictional force between the gasket 21 and the inside of the syringe cylinder 61, and therefore, slidability with the support portion 118 is improved.

The rotary-cylinder distal projection portion 119 is a part with which a fixing hook 124 (refer to FIG. 24), to be described later, provided in the cap 120 is interlocked and is formed on a portion in the circumferential direction. In an initial state before the administration, the rotary-cylinder distal projection portion 119 does not exist at the position provided with the fixing hook 124. Accordingly, the fixing hook 124 is not interlocked with the rotary-cylinder distal projection portion 119, and therefore, it is possible to remove the cap 120 from the cover member 30. After completion of the administration, unlike the initial state, the rotary-cylinder distal projection portion 119 exists at the position with which the fixing hook 124 can be interlocked since the rotary cylinder distal portion 110 is rotated with respect to the cover member 30, and therefore, the fixing hook 124 can be interlocked with the rotary-cylinder distal projection portion 119 so as to be caught therein.

As shown in FIGS. 2 and 3, the second coil spring 11 is disposed inside the cover member 30, the distal portion of the second coil spring comes into contact with a proximal surface of the cover distal portion 32, and the proximal portion of the second coil spring comes into contact with the structure 40. The second coil spring 11 is disposed in a state of being contracted in the axial direction. Accordingly, the cover member 30 is biased to the structure 40 in the distal direction.

As shown in FIG. 2, the first coil spring 12 is disposed inside the operation unit 20 and generates force of moving the operation unit 20 to the syringe 60 in the distal direction. The first coil spring 12 is in a state where the coil is contracted in a natural state free from external force. In a state where the first coil spring is forcefully stretched, the hook-shaped spring distal portion is interlocked with the spring engagement portion 108 of the structure 40, and the hook-shaped spring proximal portion 12A (refer to FIG. 14) is interlocked with the spring engagement portion 54 of the engagement plate 50 so as to be caught therein by penetrating the engagement claw insertion hole 53 of the engagement plate 50. Accordingly, the first coil spring 12 functions as an auxiliary mechanism when generating the force of moving the operation unit 20 to the structure 40 in the distal direction and discharging a liquid from the syringe 60 through the needle tube 66.

Figure 24:
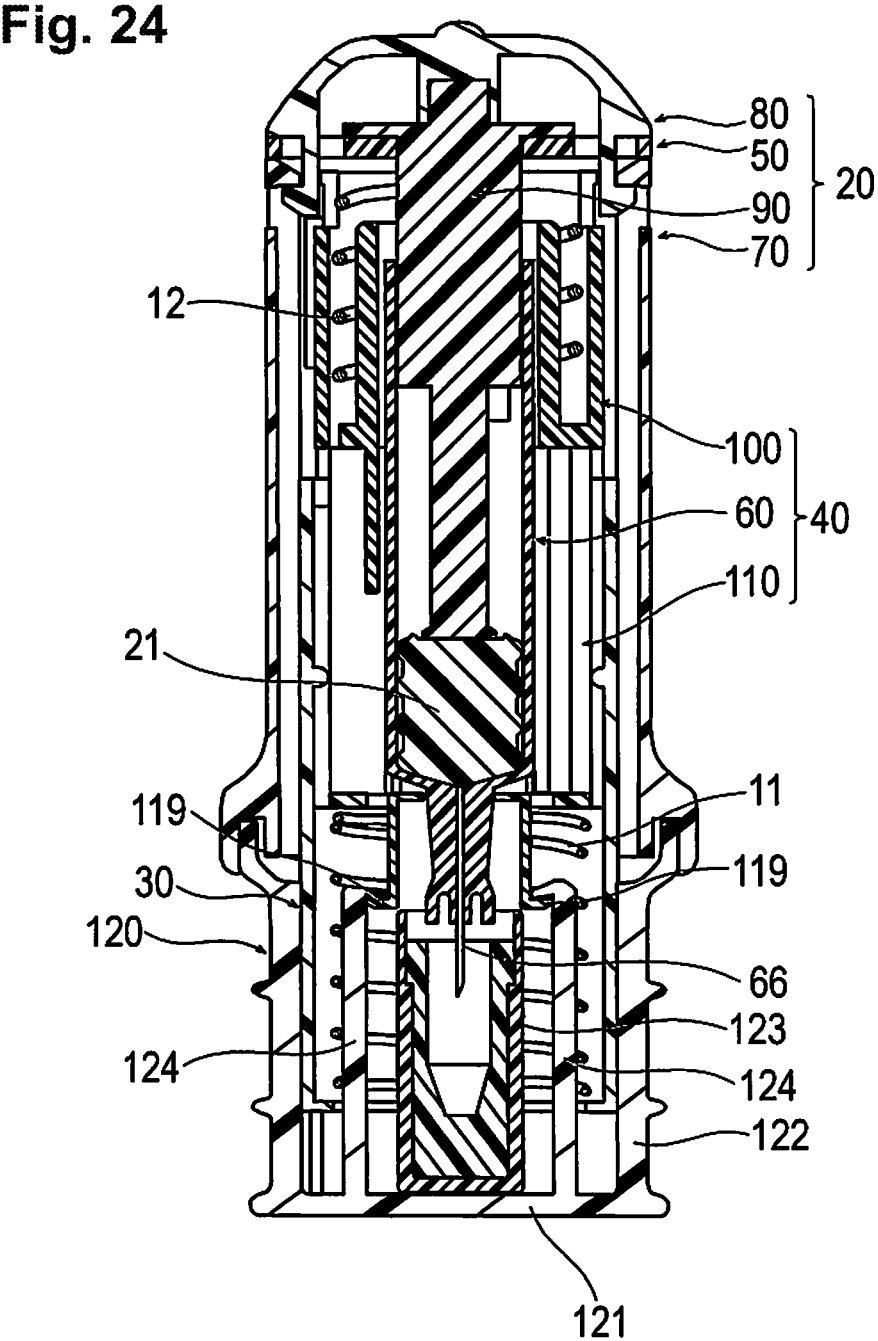
FIG. 24 is a cross-sectional view showing a state in which the liquid administration device according to the embodiment is covered with a cap.

As shown in FIGS. 2 and 24, the cap 120 is installed so as to cover the cover member 30 from the outside in an unused condition in which operation of administering the liquid has not been performed. The cap is a member formed in a bottomed cylindrical shape and includes a plate-shaped bottom portion 121, a cylindrical cap cylinder 122 that rises from the bottom portion 121, and two fixing hooks 124 that extend from the bottom portion 121 in the proximal direction. A cap 123 for a needle tube that covers the needle tube 66 is fixed to the bottom portion 121.

Constituent materials for the cover member 30, the engagement plate 50, the syringe 60, the operation unit cylinder 70, the operation unit proximal member 80, the plunger 90, the rotary cylinder proximal portion 100, the rotary cylinder distal portion 110, and the cap 120 are not particularly limited, and examples thereof include various types of resins such as polycarbonate, polyvinyl chloride, polyethylene, polypropylene, cyclic polyolefin, polystyrene, poly-(4-methylpentene-1), polyesters such as polyethylene terephthalate and polyethylene naphthalate, butadiene-styrene copolymers, and polyamide (for example, nylon 6, nylon 6-6, nylon 6-10 and nylon 12).

The constituent material of the gasket 21 and the cap 123 for a needle tube is preferably an elastic material, but is not particularly limited. Examples thereof include various rubber materials such as natural rubber, butyl rubber, isoprene rubber, butadiene rubber, styrene-butadiene rubber, and silicone rubber; various types of thermoplastic elastomers such as polyurethane, polyester, polyamide, olefin, and styrene elastomers; or mixtures thereof.

The constituent material of the needle tube 66 is not particularly limited, and examples thereof include metallic materials such as stainless steel, aluminum or aluminum alloys, and titanium or titanium alloys.

The constituent materials of the second coil spring 11 and the first coil spring 12 are not particularly limited, and examples thereof include metallic materials such as stainless steel or copper.

Next, the usage of the liquid administration device 10 according to the embodiment will be described.

First, as shown in FIGS. 1 to 3, the liquid administration device 10 in an initial unused state is prepared, and the cap 120 that covers the cover member 30 and the needle tube 66 is removed to set the liquid administration device to an initial state. Force is applied in a direction in which the structure 40 falls off from the operation unit 20 when removing the cap 120. However, it is possible to prevent the structure 40 from falling off from the operation unit 20 by bringing the movement prevention claw portion 97 that is provided in the operation unit 20 into contact with the distal end surface 106 of the resistance claw portion 105.

In the initial state, a liquid is accommodated inside the syringe cylinder 61, the operation unit 20 is positioned in the proximal direction with respect to the structure 40, and the first coil spring 12 enters a state of being extended. The spring proximal portion 12A of the first coil spring 12 is interlocked so as to be caught in a flat spring engagement surface 56 of the engagement plate 50. Furthermore, the cover member 30 is biased to the structure 40 in the distal direction by the second coil spring 11.

In the initial state, the rotation restriction unit 117 formed in the rotary cylinder distal portion 110 comes into contact with the side surface of the flange 62 to restrict rotation of the syringe cylinder 61 around the central axis in one direction, and to allow rotation of the syringe cylinder in a reversed direction.

Figure 12A:
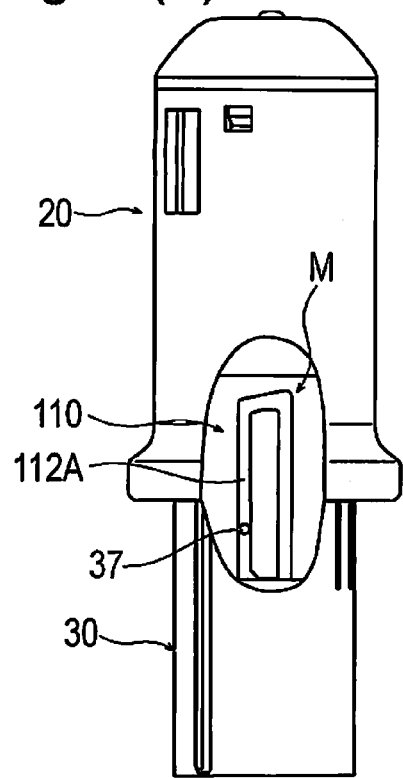
FIGS. 12(A) and 12(B) are side surface views illustrating the liquid administration device according to the embodiment in a first operation state.
Figure 12B:
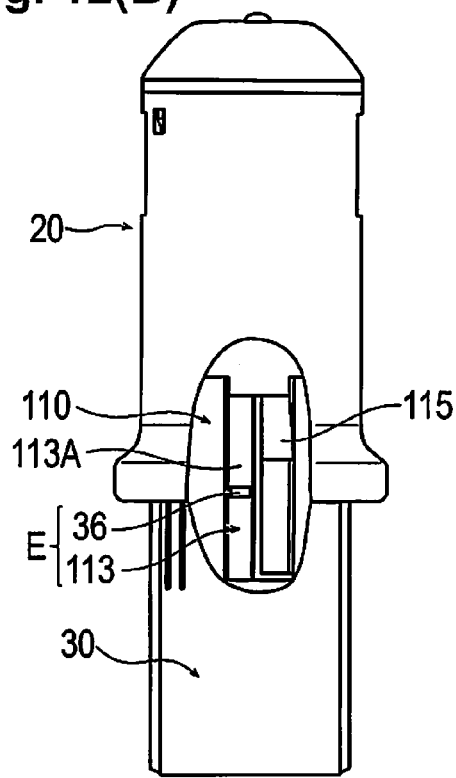

In the operation guide portion M, as shown in FIG. 12(A), the guiding convex portion 37 of the cover member 30 is positioned in the initial linear groove 112A of the rotary cylinder distal portion 110 so as to be movable along the initial linear groove 112A in the axial direction. In addition, as shown in FIG. 12(B), in the exposure restriction unit E, the safety convex portion 36 of the cover member 30 is positioned in the first safety groove 113A of the structure 40 so as to be movable along the first safety groove 113A in the axial direction. For this reason, the cover member 30 enters a state of being movable to the structure 40 in the proximal direction. Then, the cover member 30 and the structure 40 enter a first state where the safety convex portion 36 and the safety stepped portion 115 are not arranged on an identical axis parallel to the rotary axis.

In addition, as shown in FIG. 3, in the plunger restriction unit P, the plunger locking inclined portion 102 formed in the rotary cylinder proximal portion 100 is positioned on the distal side of the plunger locking projection portion 94 formed in the plunger 90 to restrict movement of the plunger 90 in the distal direction and to restrict unexpected administration of a liquid. In addition, the resistance claw portion 105 does not come into contact with the resistance projection portion 96.

In addition, the attachment portion 107 of the rotary cylinder proximal portion 100 is positioned away from the sliding surface 98 of the movement amount restriction unit 95 without being brought into contact with the sliding surface.

Figure 15:
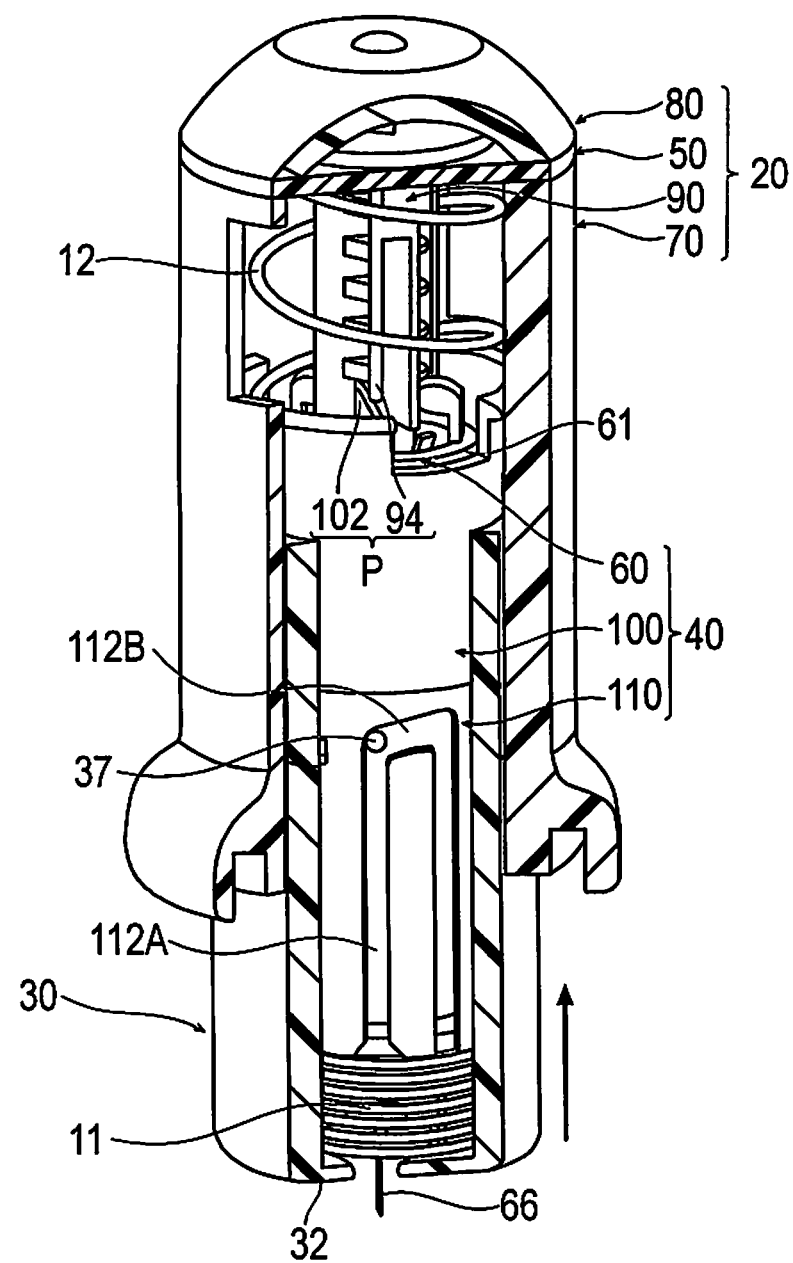
FIG. 15 is a perspective cross-sectional view that is partially cut and shows the state in which the cover member of the liquid administration device according to the embodiment is moved and an object is punctured with the needle tube.

Next, the operation unit 20 is gripped and the cover distal portion 32 of the cover member 30 is abutted on a living body. When the cover distal portion 32 of the cover member 30 is pressed to the living body, the cover member 30 enters a state of being movable to the structure 40 in the proximal direction, and therefore, as shown in FIGS. 13(A) to 15, the cover member 30 moves to the structure 40 in the proximal direction while contracting the second coil spring 11. Accordingly, the needle tube 66 protrudes from the cover member 30 in the distal direction and enters a state in which the living body is punctured with the needle tube. Note that, as shown in FIG. 15, the movement of the plunger 90 to the syringe cylinder 61 is restricted due to the plunger locking inclined portion 102 coming into contact with the plunger locking projection portion 94, and therefore, a liquid is not administered.

Figure 13A:
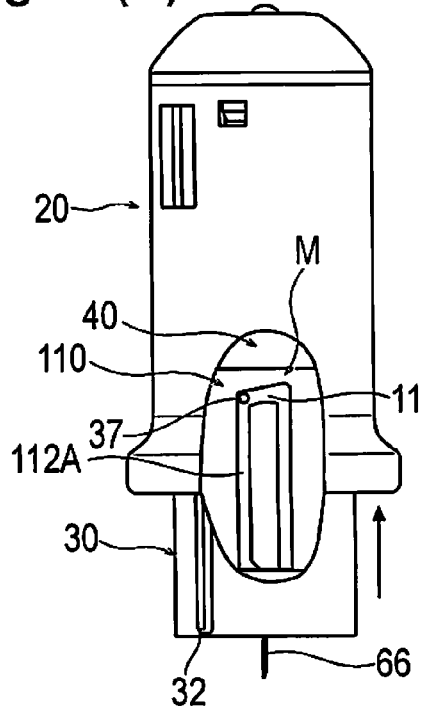
FIGS. 13(A) and 13(B) are side surface views illustrating the liquid administration device according to the embodiment in an operation state when the cover member moves to the structure.
Figure 13B:
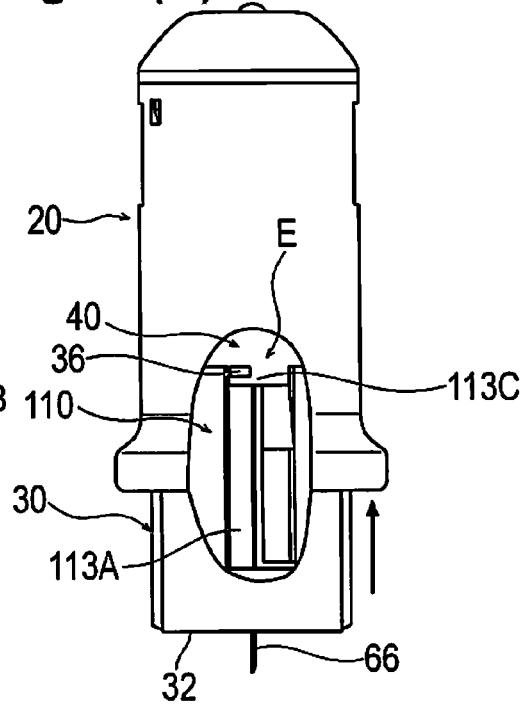

When the cover member 30 moves to the structure 40 in the proximal direction, as shown in FIG. 13(A), in the operation guide portion M, the guiding convex portion 37 of the cover member 30 is positioned in the proximal portion of the initial linear groove 112A of the structure 40, that is, on the distal side of the inclined groove 112B. In addition, as shown in FIG. 13(B), in the exposure restriction unit E, the safety convex portion 36 of the cover member 30 is positioned in the proximal portion of the first safety groove 113A of the structure 40, and is set to be movable to the proximal side communication groove 113C.

Figure 16A:
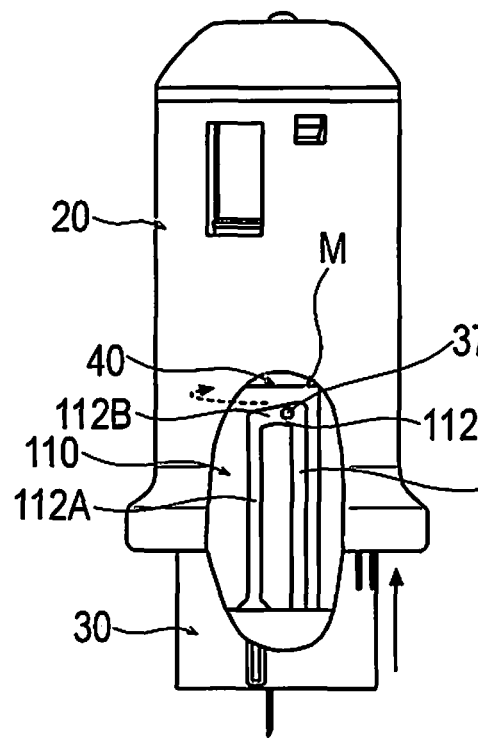
FIGS. 16(A) and 16(B) are side surface views illustrating the liquid administration device according to the embodiment in an operation state when the operation unit is further pressed after the cover member moves to the structure.
Figure 17:
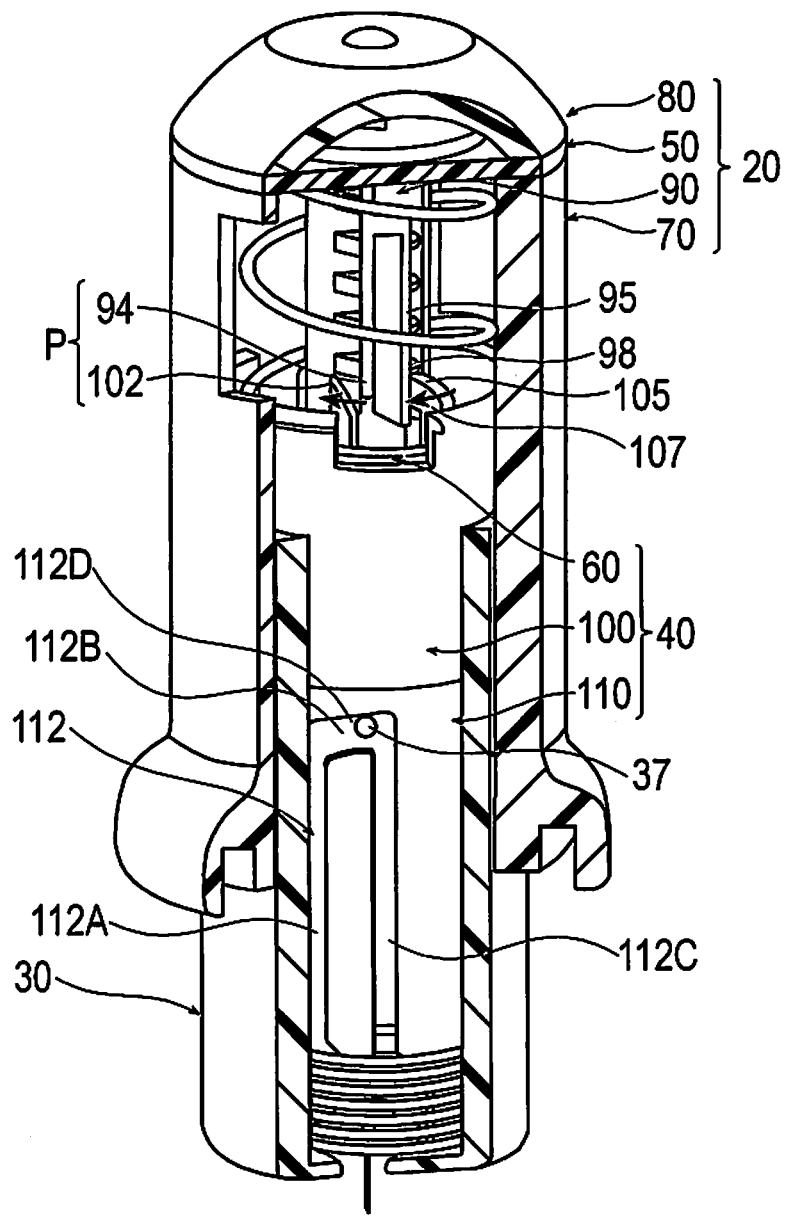
FIG. 17 is a perspective cross-sectional view that is partially cut and shows a state in which a guiding convex portion of the liquid administration device according to the embodiment stops at a holding portion for suspension.

Next, when the operation unit 20 is further pressed, as shown in FIGS. 16(A) and 17, the guiding convex portion 37 that has reached the inclined groove 112B presses the inclined groove 112B. Therefore, the guiding convex portion 37 moves in the inclined groove 112B, and the structure 40 is rotated with respect to the operation unit 20 and the cover member 30. When the structure 40 is rotated and the attachment portion 107 comes into contact with the sliding surface 98, further rotation is suppressed, and the guiding convex portion 37 enters the second state of stopping in the holding portion for suspension 112D without reaching the linear groove 112C. When the structure 40 is rotated with respect to the operation unit 20 and the cover member 30, the resistance claw portion 105 does not come into contact with the resistance projection portion 96. Therefore, there is no case where the rotation is interrupted by the contact between the resistance claw portion 105 and the resistance projection portion 96, and favorable operation can be achieved.

Figure 16B:
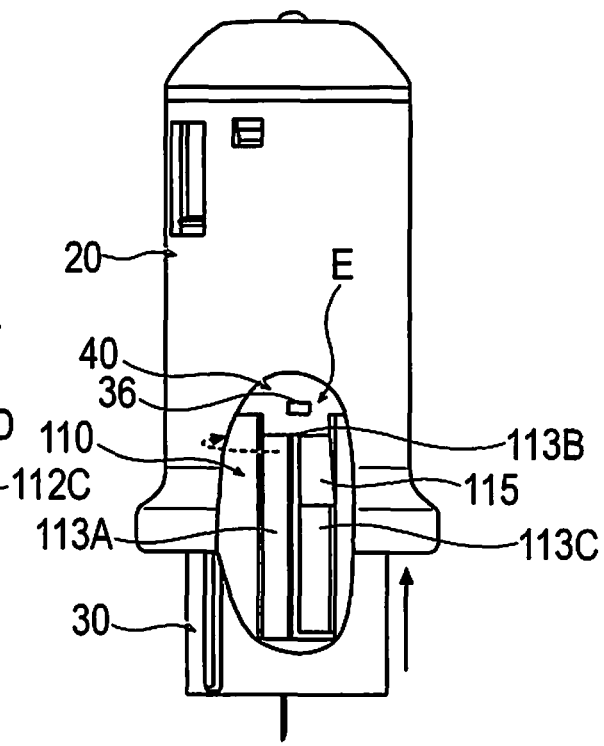

As shown in FIG. 16(B), in the exposure restriction unit E, the safety convex portion 36 stops immediately before the safety convex portion reaches the second safety groove 113B through the proximal side communication groove 113C by the rotation of the structure 40. At this time, the syringe cylinder 61 is supported by the support portion 118 provided in the structure 40 so as to be relatively rotatable. Therefore, the syringe cylinder 61 is not rotated together with the structure 40 even if the structure 40 is rotated and is maintained to be non-rotational with respect to the operation unit 20 due to the frictional force between the syringe cylinder 61 and the gasket 21 that is non-rotationally interlocked with the plunger 90. For this reason, the needle tube 66 connected to the syringe cylinder 61 is also not rotated, and therefore, it is possible to secure safety during the puncturing.

In the plunger restriction unit P, as shown in FIG. 17, the plunger locking inclined portion 102 is deviated from the position of the plunger locking projection portion 94 in the distal direction by the rotation of the structure 40 with respect to the operation unit 20, and the restriction of the movement of the plunger 90 in the distal direction is released. Therefore, it is possible to administer a liquid.

In addition, with the rotation of the structure 40 with respect to the operation unit 20, the hook-shaped spring proximal portion 12A is moved from the spring engagement surface 56 to the spring movement slope 55 to slip along the spring movement slope 55, and is moved so as to be rotated around the central axis of the operation unit 20 in the circumferential direction. Accordingly, it is possible to prevent the operability of the liquid administration device 10 from being impaired by suppressing generation of torsion of the first coil spring 12 that can occur due to the rotation of the structure 40 and suppressing unnecessary force applied on the liquid administration device 10.

Figure 18:
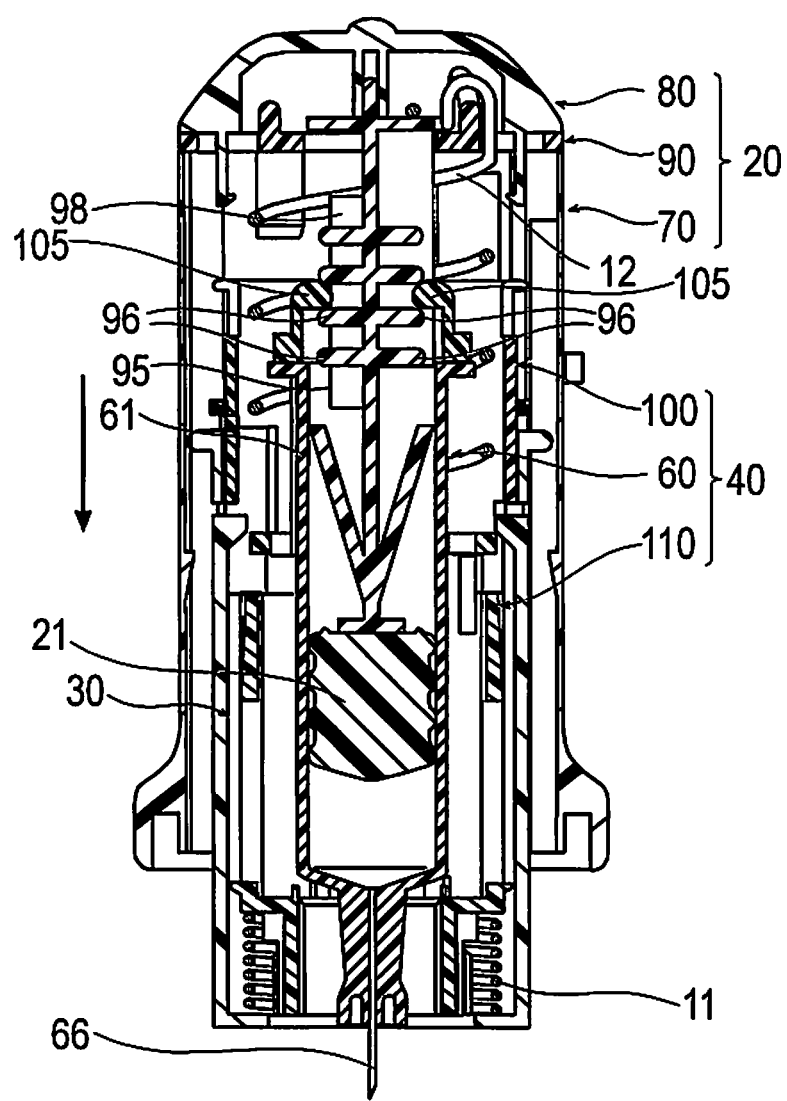
FIG. 18 is a cross-sectional view showing a state in which a liquid is administered using the liquid administration device according to the embodiment.

Next, when the operation unit 20 is further pressed, the guiding convex portion 37 of the cover member 30 cannot further move within the cam groove 112 in the proximal direction since the attachment portion 107 is brought into contact with the sliding surface 98. Therefore, the cover member 30 cannot further move to the structure 40 in the proximal direction. For this reason, the operation unit 20 moves to the structure 40 and the cover member 30 in the distal direction, and as shown in FIG. 18, the gasket 21 moves inside the syringe cylinder 61, and a liquid is administered to a living body through the needle tube 66. At this time, as shown in FIG. 16(A), in the operation guide portion M, the cover member 30 does not move to the structure 40, and therefore, the guiding convex portion 37 does not move and is positioned at the holding portion for suspension 112D of the inclined groove 112B. As shown in FIG. 16(B), also in the exposure restriction unit E, the safety convex portion 36 does not move and is positioned at a position immediately before the safety convex portion reaches the second safety groove 113B of the proximal side communication groove 113C.

In addition, administration of the liquid advances, and the attachment portion 107 slides and moves on the sliding surface 98. As shown in FIG. 18, the resistance claw portion 105 climbs over the resistance projection portions 96, which are arranged in the axial direction, while coming into contact with the resistance projection portions. In a region between two resistance projection portions 96 that is provided with no resistance projection portion 96, the resistance claw portion moves without being brought into contact with the resistance projection portions 96. When the resistance claw portion 105 climbs over the resistance projection portions 96, resistance force is generated by the resistance claw portion 105 and the resistance projection portions 96 being deformed.

The resistance claw portion 105 and the resistance projection portions 96 are symmetrically disposed across the central axis, and therefore, reaction forces generated in the direction orthogonal to the central axis are canceled by each other, and only the force parallel to the movement direction remains. Accordingly, unnecessary force is not applied on the liquid administration device 10, and favorable operation can be achieved.

When the operation unit 20 moves to the structure 40 in the distal direction, the first coil spring 12 functions as a discharge mechanism when generating force moving the operation unit 20 to the structure 40 in the distal direction and discharging a liquid from the syringe 60 through the needle tube 66 and as an auxiliary mechanism that supports the discharging.

The force that is applied for moving the gasket 21 in the syringe cylinder 61 in the distal direction is set to be the sum of biasing force (shrinkage force) F1 of the first coil spring 12, biasing force (expansive force) F2 of the second coil spring 11, and pressing force F4 of a user. Force against the force is set to be the sum of liquid discharge resistance F0, which is the sum of dynamic frictional force between the inner wall surface of the syringe cylinder 61 and the gasket 21 and needle tube discharge resistance for discharging a liquid in the syringe cylinder 61 from the needle tube 66, and contact resistance F3 when the resistance claw portion 105 comes into contact with the resistance projection portions 96. Note that the contact resistance F3 is generated only when the resistance claw portion 105 comes into contact with the resistance projection portion 96. Therefore, it is necessary to apply the pressing force F4 such that the following expression (1) is provided when the resistance claw portion 105 does not come into contact with the resistance projection portion 96, and the following expression (2) is provided when the resistance claw portion comes into contact with the resistance projection portion.

$$F1+F2+F4>F0 \qquad \text{Expression (1)}$$

$$F1+F2+F4>F0+F3 \qquad \text{Expression (2)}$$

Figure 19A:
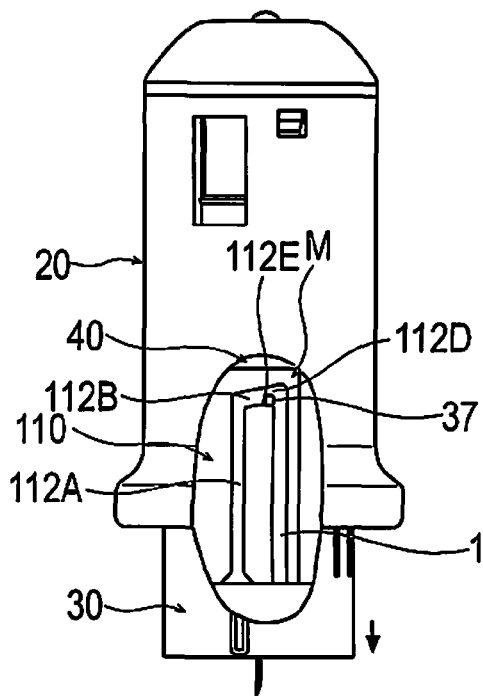
FIGS. 19(A) and 19(B) are side surface views illustrating the liquid administration device according to the embodiment in an operation state when the pressing of the operation unit is released.
Figure 19B:
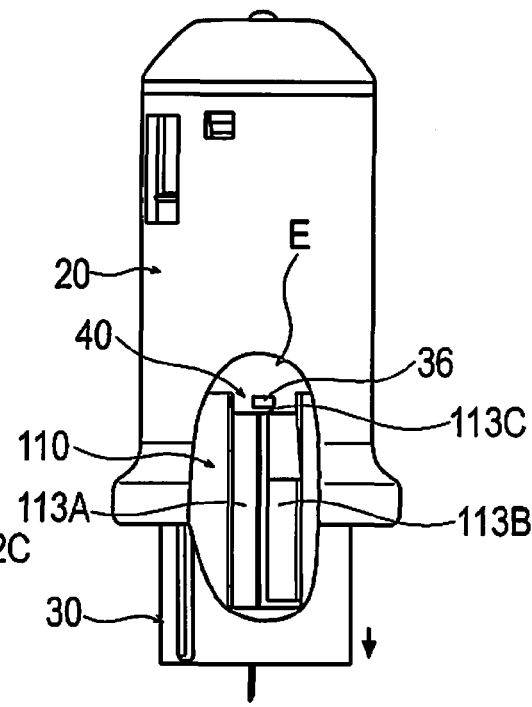

Next, when the pressing of the operation unit 20 is released in order to temporarily stop the administration of a liquid in the middle of the administration, the cover member 30 receives force with respect to the structure 40 in the distal direction due to the biasing force F1 of the first coil spring 12, and the guiding convex portion 37 comes into contact with the edge for suspension 112E of the holding portion for suspension 112D as shown in FIG. 19(A). Accordingly, the cover member 30 moves only by the movement amount of the guiding convex portion 37 in the holding portion for suspension 112D in the axial direction and does not cover the needle tube 66. For this reason, when the cover member 30 moves to the structure 40 in the distal direction, the exposure restriction unit E that controls the needle tube 66 from protruding due to the cover member 30 moving again to the structure 40 in the proximal direction is not operated. Therefore, it is possible to start the administration again. Moreover, even when the pressing of the operation unit 20 is mistakenly released in the middle of the administration, the cover member 30 hardly moves, and therefore, it is possible to prevent the administration from being difficult due to the needle tube 66 being pulled out from the living body due to the movement of the cover member 30, thereby improving the operability. In addition, when the guiding convex portion 37 comes into contact with the edge for suspension 112E of the holding portion for suspension 112D by releasing the pressing of the operation unit 20, the biasing force F2 of the second coil spring 11 is received by the engaged part between the guiding convex portion 37 and the holding portion for suspension 112D. As a result, the second coil spring 11 cannot be expanded. For this reason, the movement of the cover member 30 is restricted and the biasing force F2 of the second coil spring 11 is not applied to the movement of the gasket 21. Therefore, even a user with weak pressing force can operate the device without any burden with a small amount of force that pushes the operation unit 20. Note that the edge for suspension 112E is formed at an angle orthogonal to the axial direction of the rotary cylinder distal portion 110 or is formed so as to be inclined in a reversed direction of the inclination angle of the inclined groove 112B. Therefore, it is possible to prevent the guiding convex portion 37 from returning to the initial linear groove 112A due to the inclination of the inclined groove 112B and favorably maintain the state, in which the administration is suspended as it is. Moreover, as shown in FIG. 19(B), also in the exposure restriction unit E, the safety convex portion 36 hardly moves and is positioned at a position immediately before the safety convex portion reaches the second safety groove 113B of the proximal side communication groove 113C.

After a user stops the pressing of the operation unit 20 in the distal direction, the biasing force F2 of the second coil spring 11 and the pressing force F4 of the user are not applied to the movement of the gasket 21. Therefore, when the resistance claw portion 105 does not come into contact with the resistance projection portion 96, a liquid is automatically administered by the biasing force F1 of the first coil spring 12, and when the resistance claw portion 105 comes into contact with the resistance projection portion 96, the contact resistance F3 becomes greater and the administration of the liquid stops. In this case, it is necessary to satisfy the following expressions (3) and (4).

$$F1 > F0 \qquad \text{Expression (3)}$$

$$F1 \leq F0 + F3 \qquad \text{Expression (4)}$$

The biasing force F1 of the first coil spring 12 becomes smaller as the administration advances and the first coil spring 12 is contracted. Accordingly, the contact resistance F3 becomes smaller as the plurality of resistance projection portions 96 coming into contact with the resistance claw portion 105 are gradually reduced in size toward the proximal direction. Therefore, it is possible to set both the expressions (3) and (4) so as to be always established from the start of the administration of a liquid to the end of the administration of a liquid.

As described above, when a user stops the pressing of the operation unit 20 in the distal direction, the administration of a liquid is stopped by the resistance claw portion 105 coming into contact with the resistance projection portion 96. Accordingly, it is possible to prevent a liquid from being automatically administered without pressing the operation unit 20 in the distal direction by the user when administering the liquid. Accordingly, it is possible to administer a liquid by the intention of the user. For example, it is possible to administer a liquid at a pace of the user, or it is possible to suspend the administration of a liquid by stopping the pressing when it is necessary to suspend the administration of the liquid.

Note that it is possible to stop the administration of a liquid in both cases where the resistance claw portion 105 comes into contact with the resistance projection portion 96 or does not come into contact with the resistance projection portion, after a user stops the pressing of the operation unit 20 in the distal direction. In this case, it is necessary to satisfy the following expressions (5) and (6) instead of the expressions (3) and (4).

$$F1 \leq F0 \qquad \text{Expression (5)}$$

$$F1 \leq F0 + F3 \qquad \text{Expression (6)}$$

In addition, the device may also be set such that the administration of a liquid is continued in both cases where the resistance claw portion 105 comes into contact with the resistance projection portion 96 or does not come into contact with the resistance projection portion, after a user stops the pressing of the operation unit 20 in the distal direction. In this case, it is necessary to satisfy the following expressions (7) and (8) instead of the expressions (3) and (4).

$$F1 > F0 \qquad \text{Expression (7)}$$

$$F1 > F0 + F3 \qquad \text{Expression (8)}$$

Figure 20A:
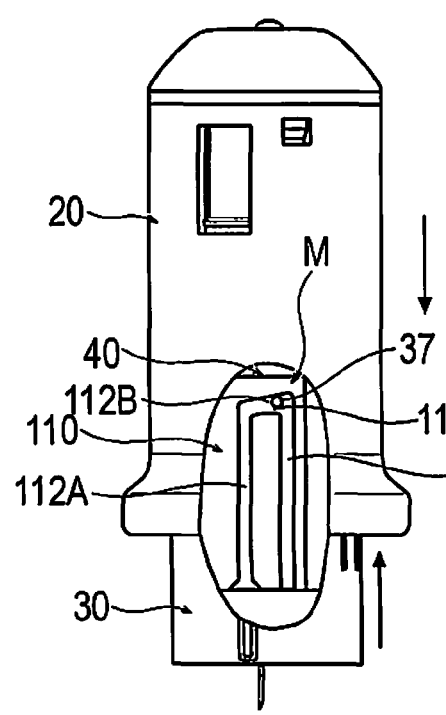
FIGS. 20(A) and 20(B) are side surface views illustrating the liquid administration device according to the embodiment in an operation state when the operation unit is pressed again after a temporary stop.
Figure 20B:
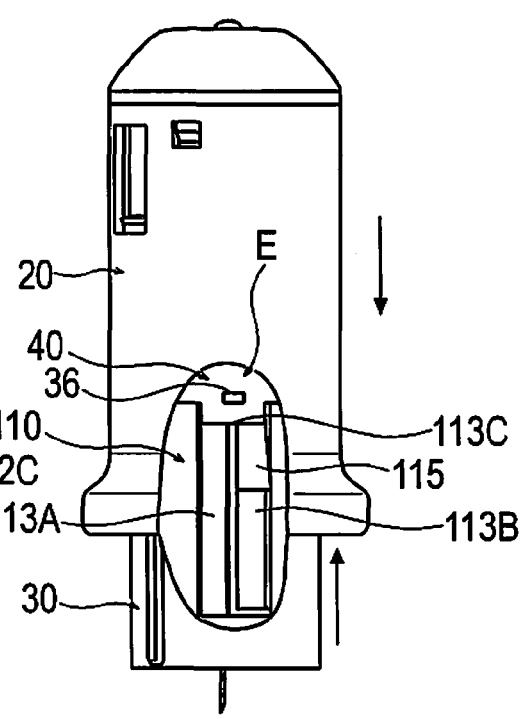

In a case where the administration of a liquid temporarily stops, when the operation unit 20 is gripped again and a living body is punctured with the needle tube 66 to press the operation unit 20 in the distal direction, the guiding convex portion 37 of the cover member 30 cannot move from the holding portion for suspension 112D as shown in FIG. 20(A) since the attachment portion 107 is brought into contact with the sliding surface 98. For this reason, the operation unit 20 moves to the structure 40 and the cover member 30 in the distal direction, the gasket 21 moves inside the syringe cylinder 61, and a liquid is administered to a living body through the needle tube 66.

Moreover, it is possible to repeat the above-described stopping and restarting of the administration of a liquid plural times in accordance with the situation. Meanwhile, it is possible to intentionally perform the administration to different areas by being divided into plural times.

When the liquid inside the syringe cylinder 61 is absent and the administration of the liquid is completed, as shown in FIG. 21, the noise generation claw 82 provided in the operation unit 20 is engaged with the noise generation hole 101 provided in the structure 40. When the noise generation claw 82 is engaged with the noise generation hole 101, the elastically deformed noise generation claw 82 is engaged with the noise generation hole 101 in a manner of being returned to its original shape, and the noise generation claw 82 comes into contact with the rotary cylinder proximal portion 100 formed with the noise generation hole 101 to generate noise. It is possible to acoustically check the completion of the administration of a liquid through the generation of noise.

When the movement amount of the operation unit 20 with respect to the structure 40 reaches a movement amount for the completion of the administration and the administration of a liquid is completed, the sliding surface 98 sliding on the attachment portion 107 reaches the accommodation portion 99. When the sliding surface 98 reaches the accommodation portion 99, the attachment portion 107 does not come into contact with the sliding surface 98 and the restriction due to the movement amount restriction unit 95 is released Therefore, the structure 40 can rotate with respect to the operation unit 20. Accordingly, as shown in FIG. 22(A), the guiding convex portion 37 moves in the inclined groove 112B and reaches the linear groove 112C, and the structure 40 is rotated with respect to the operation unit 20. Therefore, the resistance claw portion 105 having the attachment portion 107 is accommodated in the accommodation portion 99. When the structure 40 is rotated with respect to the operation unit 20, the resistance claw portion 105 is not already brought into contact with the resistance projection portion 96, and therefore, the rotation is not interrupted. When the resistance claw portion 105 is accommodated in the accommodation portion 99, the movement amount restriction unit 95 is positioned on the distal side of the resistance claw portion 105, and therefore, it is possible to prevent the structure 40 from being pulled out from the operation unit 20 in the distal direction.

In a state where the administration is completed, in the exposure restriction unit E, the safety convex portion 36 is positioned in the proximal portion of the second safety groove 113B as shown in FIG. 22(B). At this time, the cover member 30 and the structure 40 enter the third state where the safety convex portion 36 and the safety stepped portion 115 are arranged on an identical axis parallel to the rotary axis.

From this state, when the operation unit 20 is gripped and the cover distal portion 32 is separated from the skin, as shown in FIGS. 23(A) and 23(B), the cover member 30 moves to the structure 40 in the distal direction due to the biasing force of the second coil spring 11, and the needle tube 66 is accommodated in the cover member 30. Accordingly, as shown in FIG. 23(A), the guiding convex portion 37 moves in the linear groove 112C in the proximal direction. In the exposure restriction unit E, as shown in FIG. 23(B), the safety convex portion 36 moves in the second safety groove 113B in the distal direction and is deformed and climbs over the safety slope 115A of the safety stepped portion 115 while slipping along the safety slope thereof to reach the distal portion of the safety stepped portion 115. The movement amount at this time corresponds to an exposure restriction operation amount when the cover member 30 is shifted from the exposure position to the protection position. Once the safety convex portion 36 climbs the safety stepped portion 115, the movement of the safety convex portion 36 in the proximal direction in the second safety groove 113B is suppressed by the safety wall surface 115B. Therefore, the cover member 30 cannot move to the structure 40 in the proximal direction and enters a state where the exposure restriction unit E is operated. When the cover member enters the state where the exposure restriction unit E is operated, the needle tube 66 cannot protrude from the cover member 30 again, and therefore, it is possible to improve safety by suppressing erroneous puncturing due to the needle tube 66.

Thereafter, as shown in FIG. 24, the cap 120 is attached to the cover member 30. At this time, unlike the initial state, the rotary cylinder distal portion 110 is rotated with respect to the cover member 30. Therefore, the fixing hook 124 of the cap 120 is caught in the rotary-cylinder distal projection portion 119 of the rotary cylinder distal portion 110 and the cap 120 is undetachably attached to the rotary-cylinder distal projection portion, thereby securing safety.

As described above, the liquid administration device 10 according to the present embodiment is used for administering a liquid into a living body and includes an operation unit 20 for performing operation by being gripped, a structure 40 that includes a syringe 60 (accommodation body) capable of accommodating the liquid therein and a needle tube 66 communicatable with the inside of the syringe 60 and is relatively rotatable with respect to the operation unit 20 and movable in an axial direction of the rotation, a cover member 30 movable between a protection position at which the needle tube 66 is covered and an exposure position from which the needle tube 66 is exposed, a second coil spring 11 (biasing member) that biases the cover member 30 in the distal direction, an exposure restriction unit E that restricts movement of the cover member 30 to the exposure position when the cover member 30 moves from the exposure position to the protection position using biasing force of the second coil spring 11 and the movement amount of the cover member 30 with respect to the structure 40 reaches a predetermined exposure restriction operation amount, and a movement amount restriction unit 95 which restricts the movement amount of the cover member 30 such that the movement amount by which the cover member 30 is movable to the structure 40 in the distal direction using the biasing force of the second coil spring 11 does not reach the exposure restriction operation amount until the movement amount of the operation unit 20 with respect to the structure 40 in the distal direction reaches a predetermined movement amount for completion of the administration. For this reason, in the liquid administration device 10, safety can be secured by providing the cover member 30 that covers the needle tube 66 in a manner in which the needle tube 66 can be exposed, and interruption of operation due to movement of the cover member 30 during the administration can be suppressed by a movement amount restriction unit 95 restricting the movement amount of the cover member 30. Therefore, operability can be improved. Furthermore, with the provision of the movement amount restriction unit 95, the movement amount by which the cover member 30 is movable to the structure 40 in the distal direction does not reach the exposure restriction operation amount until the movement amount of the operation unit 20 with respect to the structure 40 in the distal direction reaches the movement amount for completion of the administration. For this reason, the movement of the cover member 30 to the exposure position is not restricted until the administration is completed and the movement amount of the operation unit 20 reaches the exposure restriction operation amount, and it is possible to resume administration even if the administration operation is suspended in the middle of the administration.

In addition, in the liquid administration device 10 according to the present embodiment, the structure 40 is relatively rotatable with respect to the operation unit 20 and the cover member 30. Therefore, arrangement can be made such that a plurality of functions, such as the above-described movement amount restriction unit 95, the exposure restriction unit E that restricts exposure of the needle tube 66 after the administration, and the plunger restriction unit P that restricts the plunger 90 so as not to be pressed until a condition is satisfied, are operated at different rotational positions, and thus, the functions do not interfere with each other. When the structure is constituted so as not to be rotated with respect to the operation unit and the cover member, the device can be devised such that one member climbs over another member while the members are brought into contact with each other so as not to operate a function depending on the condition in order to exhibit all functions on linear motion. However, in this case, there are concerns that operability may deteriorate due to increased resistance when pressing the operation unit and the accuracy of each function may decrease. In contrast, since the structure 40 is relatively rotatable with respect to the operation unit 20 and the cover member 30 as in the present embodiment, it is possible to provide a plurality of functions without interfering with each other. Therefore, it is possible to improve the operability by reducing the resistance when pressing the operation unit 20 and to improve the accuracy of each function.

In addition, in the liquid administration device 10 according to the present embodiment, the cover member 30 exists at a protection position at which the needle tube 66 is covered in an initial state, and therefore, it is possible to reduce fear when inserting the needle tube 66 before injecting a drug solution. Moreover, it is possible to restrict re-exposure of the needle tube 66 being pulled out in the middle of operation by covering the needle tube with the cover member 30, and to reduce mental pain in which the expensive medicine cannot be used for injection again.

In addition, the liquid administration device 10 can be smoothly operated through rotary motion using the relationship between the groove and the convex portion and can be operated with weak force, thereby facilitating the administration. Note that, in the case of the linear motion, it is difficult to obtain the same effect as that of the rotary embodiment of the present invention with a small amount of force on the assumption that there is a step over which it is necessary to climb as described above.

In addition, in the liquid administration device 10 according to the present embodiment, the exposure restriction unit E includes a safety convex portion 36 (first engagement portion) that is formed in any one of the structure 40 and the cover member 30, and a safety stepped portion 115 (second engagement portion) which is formed in the other one of the structure and the cover member and can be engaged with the safety convex portion 36. The structure 40 and the cover member 30 include an operation guide portion M in which a first state where positions of the safety convex portion 36 and the safety stepped portion 115 in a rotational direction are not coincident with each other is shifted to a third state where the positions of the safety convex portion 36 and the safety stepped portion 115 in the rotational direction are coincident with each other, via a second state through relative rotation. The movement amount restriction unit 95 includes an attachment portion 107 that is provided in any one of the operation unit 20 and the structure 40 and a sliding surface 98 that is provided in the other one of the operation unit and the structure, that extends in the axial direction, and that slidably comes into contact with the attachment portion 107 in the axial direction. The liquid administration device 10 is constituted such that, in the first state, the attachment portion 107 is positioned away from the sliding surface 98, and in the second state, the attachment portion 107 is slidable along the sliding surface 98 while restricting the relative rotation between the operation unit 20 and the structure 40 and restricting the shift to the third state by bringing the attachment portion 107 into contact with the sliding surface 98, and the attachment portion 107 sliding on the sliding surface 98 is accommodated in an accommodation portion 99 that is formed on a side in a movement direction of the attachment portion 107 with respect to the sliding surface 98 and can receive the attachment portion 107. As a result, the operation unit 20 and the structure 40 relatively rotate and enter the third state where the cover member 30 is movable to the structure 40 in the distal direction by the exposure restriction operation amount. For this reason, the shift to the third state is restricted since the second state is maintained while the administration of a liquid is performed by the attachment portion 107 sliding on the sliding surface 98. Therefore, the restriction of the movement of the cover member 30 to the exposure position using the exposure restriction unit E that becomes possible through the shift to the third state is not performed, and therefore, it is possible to suspend and resume the administration. After the administration is completed and the attachment portion 107 is accommodated in the accommodation portion 99, the state of the device enters the third state where the cover member 30 is movable by the exposure restriction operation amount, the cover member 30 is moved to the protection position, and the safety convex portion 36 and the safety stepped portion 115 are engaged with each other. As a result, it is possible to secure safety by restricting the movement of the cover member 30 so as not to move to the exposure position again.

In addition, in the liquid administration device 10 according to the present embodiment, the operation guide portion M has a cam groove 112 in any one of the structure 40 and the cover member 30, and a guiding convex portion 37 (convex portion) that is accommodated in the cam groove 112 and moves along the cam groove 112 in the other one of the structure and the cover member. The cam groove 112 includes an initial linear groove 112A (first groove portion) that is used for relatively moving the structure 40 and the cover member 30 in the axial direction in the first state, an inclined groove 112B (second groove portion) that communicates with the initial linear groove 112A and is inclined in the axial direction for relatively rotating the structure 40 and the cover member 30 so as to shift the state of the structure and the cover member from the first state to the third state, and a linear groove 112C (third groove portion) that communicates with the inclined groove 112B and is used for engaging the safety convex portion 36 and the safety stepped portion 115 by relatively moving the structure 40 and the cover member 30 in the axial direction in the third state. In the second state, the guiding convex portion 37 is positioned in the inclined groove 112B. For this reason, it is possible to shift the state of the device between the first state, the second state, and the third state by moving the guiding convex portion 37 along the cam groove 112, and to restrict the movement of the cover member 30 to the structure 40 in the axial direction, in the second state, by positioning the guiding convex portion 37 in the inclined groove 112B, which is inclined, to enter the second state. Accordingly, when the administration of a liquid is suspended without being completed and the state of the device enters the second state, the movement amount by which the cover member 30 is movable to the structure 40 in the distal direction does not reach the exposure restriction operation amount. Therefore, it is possible to resume the administration even if the administration operation is suspended in the middle of the administration since the movement of the cover member 30 to the exposure position is not restricted by the exposure restriction unit E.

In addition, in the liquid administration device 10 according to the present embodiment, a holding portion for suspension 112D that makes the guiding convex portion 37 movable in the axial direction by less than the exposure restriction operation amount in the second state, is formed in the inclined groove 112B. For this reason, when the administration is suspended, the guiding convex portion 37 can move in the holding portion for suspension 112D by less than the exposure restriction operation amount, and the cover member 30 can move in a direction in which the needle tube 66 is covered therewith, and therefore, it is possible to improve safety during the suspension.

In addition, in the liquid administration device 10 according to the present embodiment, an edge for suspension 112E that is orthogonal to the axial direction or is inclined in an opposite direction to a direction where the inclined groove 112B is inclined in the axial direction and by which the guiding convex portion 37 brought into contact therewith is held in the second state is formed at an edge of the holding portion for suspension 112D. For this reason, the guiding convex portion 37 is held by the edge for suspension 112E when suspending the administration, and therefore, it is possible to suppress returning of the guiding convex portion 37 to the initial linear groove 112A due to the inclination of the inclined groove 112B and to favorably maintain the state where the administration is suspended as it is.

Figure 25A:
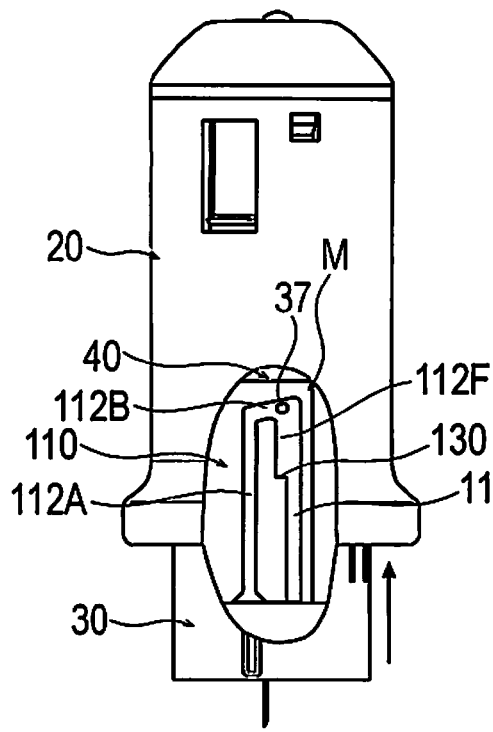
FIGS. 25(A) and 25(B) are side surface views illustrating an operation state of a modification example of the liquid administration device according to the embodiment where a holding portion for suspension is formed lengthwise in a stepped shape.
Figure 25B:
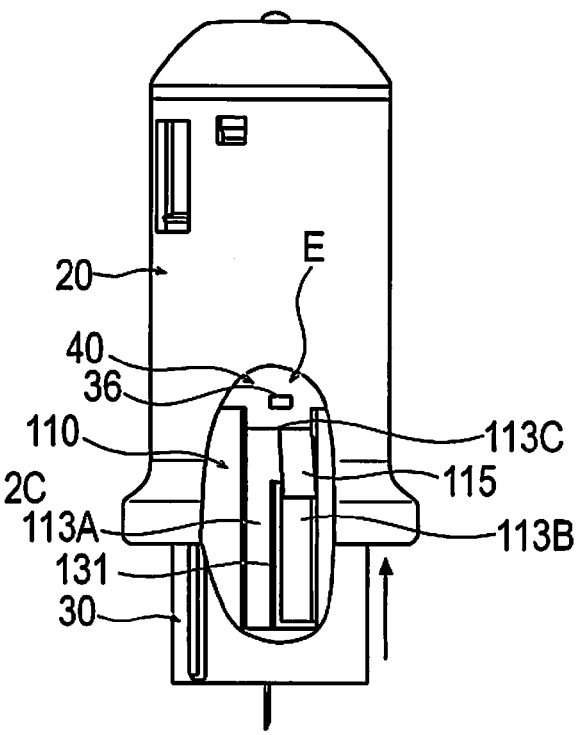
Figure 26A:
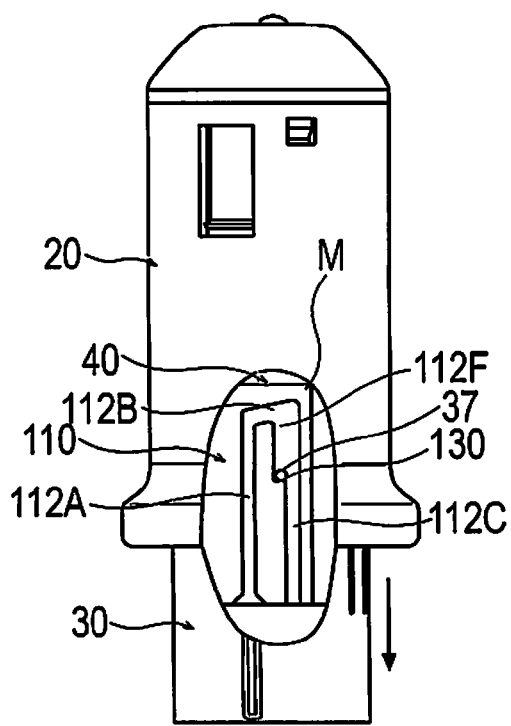
FIGS. 26(A) and 26(B) are side surface views illustrating the modification example of the liquid administration device according to the embodiment in an operation state when the administration temporarily stops.
Figure 26B:
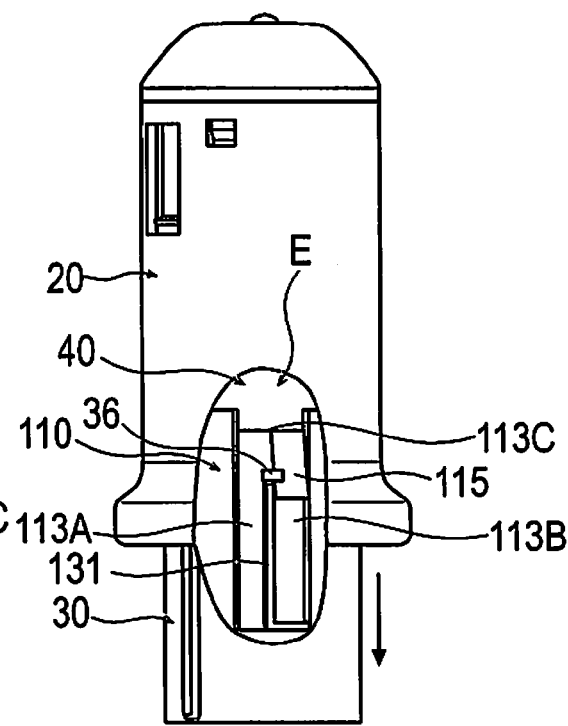
Figure 29:
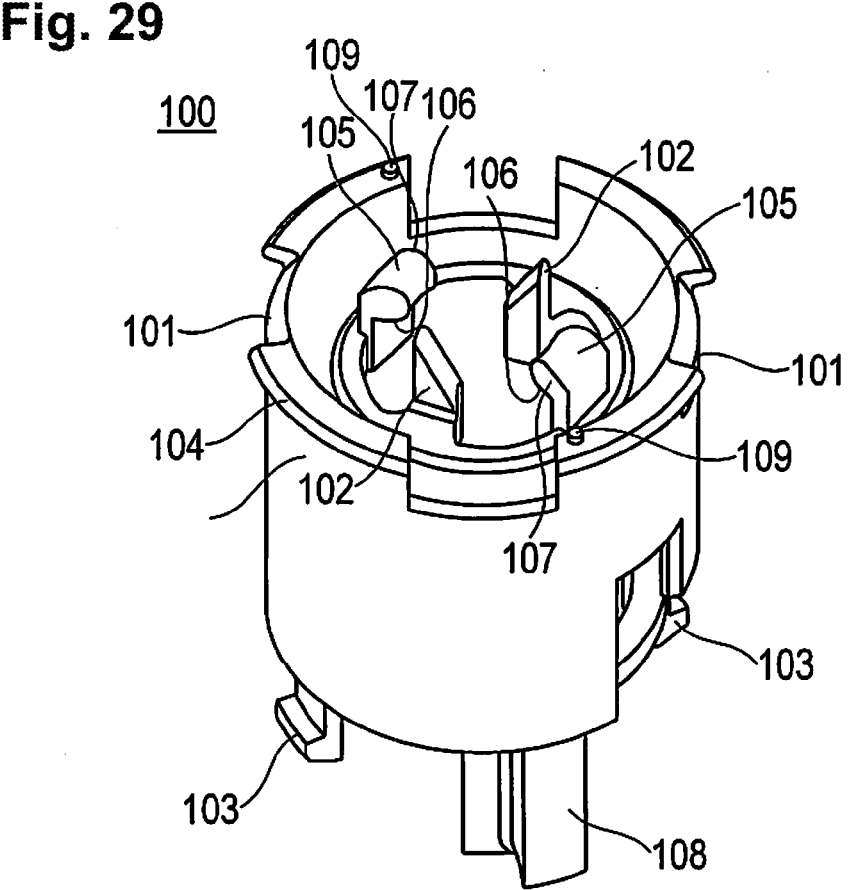
FIG. 29 is a perspective view showing a rotary cylinder proximal portion of still another modification example of the liquid administration device according to the embodiment.
Figure 30:
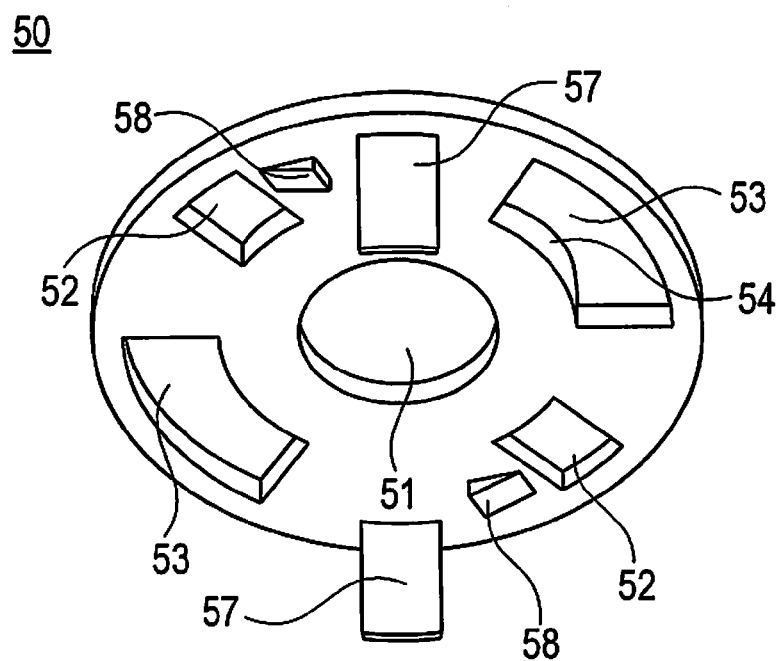
FIG. 30 is a perspective view showing an engagement plate of still another modification example of the liquid administration device according to the embodiment.

Note that the present invention is not limited only to the above-described embodiments, and various modifications can be made by those skilled in the art within technical ideas of the present invention. For example, as in a modification example shown in FIGS. 25(A) and 25(B), a holding portion for suspension 112F of the inclined groove 112B may be formed lengthwise in a stepped shape in the distal direction from the inclined groove 112B. Note that parts having the identical functions as those in the above-described embodiment are identified by the same reference numerals throughout and the detailed descriptions are not repeated. With the holding portion for suspension formed lengthwise from the inclined groove 112B in the distal direction, when the administration temporarily stops, as shown in FIG. 26(A), the cover member 30 moves in the distal direction and the needle tube 66 is covered with the cover member 30, and thus, it is possible to improve safety. Note that, the length of the inclined groove 112B in the distal direction is set to be less than the exposure restriction operation amount, that is, a length at which the safety convex portion 36 does not climb the safety stepped portion 115 so as to preclude the movement of the cover member 30 due to the exposure restriction unit E operated when the administration temporarily stops, as shown in FIG. 26(B). In the exposure restriction unit E, it is preferable that a rib 131 between the first safety groove 113A and the second safety groove 113B is not formed on the proximal side of the rotary cylinder distal portion 110, or the first safety groove 113A or the second safety groove 113B is formed widely, such that the safety convex portion 36 is movable in the distal direction in the second state where the guiding convex portion 37 is positioned in the holding portion for suspension 112F.

When resuming the administration, it is possible to administer a liquid again by moving the cover member 30 to the structure 40 in the proximal direction and puncturing a living body with the needle tube 66 while moving the guiding convex portion 37 within the holding portion for suspension 112F by gripping the operation unit 20 and pressing the cover member 30 to the skin.

In addition, as in another modification example shown in FIGS. 27(A) and 27(B), a holding portion for suspension 112G of the inclined groove 112B may be formed parallel to the linear groove 112C and not in the stepped shape communicating with the linear groove 112C. Also with such a holding portion for suspension 112G, it is possible to suspend administration of a liquid by holding the guiding convex portion 37.

In addition, as in still another modification example shown in FIG. 28, the part of a plunger 140 which comes into contact with the resistance claw portion 105 may be a flat contact surface 141 instead of being a projection shape. It is possible to arbitrarily change contact resistance F3 with respect to the resistance projection portion 96 depending on parts by making the surface roughness of the flat contact surface 141 vary depending on parts, coating the contact surface with different materials depending on parts, forming the contact surface into a tapered shape such that the distance from the resistance claw portion 105 varies, and changing the width of the surface of the contact surface along the axial direction such that the area coming into contact with the resistance claw portion 105 varies, for example. The contact surface 141 continuously comes into contact with the resistance projection portion 96 instead of being intermittent during the administration. It is easy to establish the above-described expression (2) or (4) at all times from the start of the administration of a liquid to the end of the administration of the liquid by setting the contact resistance F3 between the resistance projection portion 96 and the contact surface 141 to become continuously smaller toward the proximal side of the contact surface. Furthermore, if the difference between the contact resistance F3 and the biasing force F1 due to the first coil spring 12 is maintained to be constant when the operation unit 20 moves to the structure 40 in the distal direction, it is possible to administer a liquid at a constant administering rate using constant pressing force. Therefore, it is possible to improve accuracy and safety of the administration. In addition, the contact resistance F3 may be generated through contact between the sliding surface 98 and the attachment portion 107.

In addition, as shown in FIG. 28, the plunger 140 may be formed with a guiding slope 142 (slope) for guiding the resistance claw portion 105 to the accommodation portion 99 on the proximal side of the contact surface 141 that comes into contact with the resistance claw portion 105 (contact portion). When the movement amount of the operation unit 20 to the structure 40 in the distal direction in the second state reaches a predetermined movement amount for the completion of the administration and the administration of a liquid is completed, the guiding slope 142 plays a role of coming into contact with the resistance claw portion 105 and guiding the resistance claw portion 105 to the accommodation portion 99 along the inclination. The state of the device is easily shifted from the second state to the third state by forming such a guiding slope 142. Note that the guiding slope 142 may be formed in the plunger 90 shown in FIG. 7.

In addition, as in still other modification examples shown in FIGS. 29 to 31(B), two rotating contact portions 109 with a convex shape may be formed on a proximal surface of the rotary cylinder proximal portion 100, and two inclined portions 58 that can come into contact with the rotating contact portions 109 may be formed on a distal end surface of the engagement plate 50. The two rotating contact portions 109 are provided at positions opposite to each other across a central axis of the rotary cylinder proximal portion 100 and protrude in the proximal direction. The two inclined portions 58 are provided at positions opposite to each other across a central axis of the engagement plate 50 and are formed so as to be inclined along the circumferential direction.

Figure 31A:
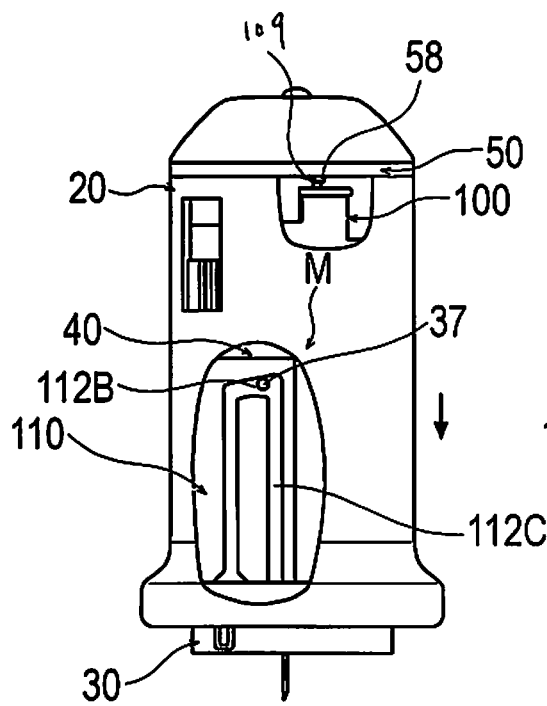
FIGS. 31(A) and 31(B) are side surface views illustrating an operation state of still another modification example of the liquid administration device according to the embodiment.
Figure 31B:
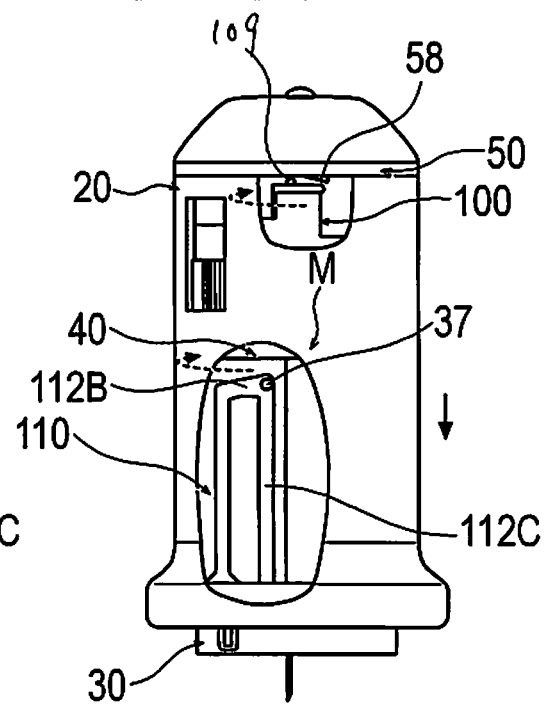

When the administration is performed using a liquid administration device including the above-described rotating contact portions 109 and the inclined portions 58, as shown in FIG. 31(A), the rotating contact portion 109 of the rotary cylinder proximal portion 100 moves in the proximal direction and comes into contact with the inclined portion 58 of the engagement plate 50 immediately before the restriction of the rotation of the structure 40 with respect to the operation unit 20 using the movement amount restriction unit 95 is released as the administration is about to be completed. When the rotating contact portion 109 comes into contact with the inclined portion 58, as shown in FIG. 31(B), the rotating contact portion 109 moves along the circumferential direction by slipping along the inclination of the inclined portion 58, and therefore, the structure 40 having the rotary cylinder proximal portion 100 is rotated with respect to the operation unit 20 having the engagement plate 50. For this reason, even if the pressing by a user is insufficient during the administration and the rotational force for rotating the structure 40 using the operation guide portion M is insufficient, it is possible to reliably move the guiding convex portion 37 to the linear groove 112C at the time of completion of administration by providing the rotating contact portion 109 and the inclined portion 58. When the administration is completed in a state where the guiding convex portion 37 cannot move to the linear groove 112C, the plunger 90 is completely pulled down by the shrinkage force of the first coil spring 12. Therefore, even if the operation unit 20 is pressed thereafter, it is impossible to further rotate the structure 40 with respect to the operation unit 20. In such a state, it is impossible to move the guiding convex portion 37 to the linear groove 112C and to move the cover member 30 from the exposure position to the protection position. However, with provision of the above-described rotating contact portion 109 and the inclined portion 58, it is possible to cover the needle tube 66 by reliably rotating the structure 40 with respect to the operation unit 20, moving the guiding convex portion 37 to the linear groove 112C, and reliably moving the cover member 30 from the exposure position to the protection position, thereby improving safety.

In addition, the inclined portion 58 is provided in the operation unit 20 and the rotating contact portion 109 is provided in the structure 40. Therefore, biasing force (shrinkage force) F1 of the first coil spring 12 applied between the operation unit 20 and the structure 40 directly affects the operation of pressing the rotating contact portion 109 to the inclined portion 58 and rotating the structure 40. At this time, biasing force (expansive force) F2 of the second coil spring 11 applied between the structure 40 and the cover member 30 does not directly affect relative movement of the rotating contact portion 109 and the inclined portion 58. Therefore, even if the pressing by a user is weakened, the guiding convex portion 37 comes into contact with the edge for suspension 112E, and the second coil spring 11 cannot be expanded, it is possible to rotate the structure 40 using the biasing force F1 of the first coil spring 12, and even a user with weak pressing force can operate the device without any burden.

Note that the slope may be provided in another part of the operation unit 20 and the contact portion coming into contact with the slope may be provided in another portion of the structure 40. In addition, the slope may be provided in the structure and the contact portion may be provided in the operation unit 20.

In addition, the part to which the contact resistance F3 is imparted may not be between the plunger 90 and the rotary cylinder proximal portion 100, and for example, may be between the inner wall surface of the syringe cylinder 61 and the gasket 21.

In addition, in the above-described embodiment, the needle tube 66 communicates with the syringe cylinder 61 in advance. However, the needle tube 66 may be a double ended needle that is provided so as not to communicate with the syringe cylinder and is stuck into the syringe cylinder in use so as to communicate therewith.

In addition, in the above-described embodiment, the structure 40 includes the rotary cylinder proximal portion 100 and the rotary cylinder distal portion 110, but the structure may be formed of one member. In addition, the structure and the syringe cylinder may be integrally formed.

In addition, in the above-described embodiment, the sliding surface 98 is formed in the plunger 90 and the attachment portion 107 coming into contact with the sliding surface 98 is formed in the rotary cylinder proximal portion 100. The members formed with the sliding surface and the attachment portion are not particularly limited as long as the members are relatively rotated and move along the axial direction. Accordingly, the sliding surface may be formed in any one of the operation unit cylinder and the structure, and the attachment portion may be formed in the other one. The sliding surface may be a wall surface of a rib formed to protrude, or a wall surface inside a groove.

In addition, the first coil spring 12 may not be provided. In addition, the resistance projection portion 96 and the resistance claw portion 105 which apply the contact resistance F3 may not be provided and the contact resistance F3 may not be applied.

The invention claimed is:

1. A liquid administration device for administering a liquid into a living body, comprising:
   a structure that includes an accommodation body configured to accommodate the liquid therein and a needle tube communicatable with an inside of the accommodation body, the structure being rotatable relative to the operation unit and movable in an axial direction of rotation;
   an operation unit configured to move in a distal direction with respect to the structure by a predetermined distance to a location at which administration of the liquid is completed;
   a cover member that is movable between a protection position at which the needle tube is covered and an exposure position at which the needle tube is exposed;
   a biasing member that biases the cover member in the distal direction, wherein the cover member is moveable from the exposure position to the protection position via a biasing force of the biasing member;
   an exposure restriction unit configured to restrict movement of the cover member to the exposure position after the cover member moves in the distal direction with respect to the structure by a predetermined exposure restriction operation distance; and
   a movement restriction unit configured to restrict the movement of the cover member such that the cover member does not move in the distal direction with respect to the structure by the exposure restriction operation distance due to the biasing force of the biasing member until the operation unit first moves in the distal direction with respect to the structure by the predetermined distance to the location at which administration of the liquid is completed.

2. The liquid administration device according to claim 1, wherein the exposure restriction unit includes:
   a first engagement portion that is formed in one of the structure and the cover member; and
   a second engagement portion that is formed in the other one of the structure and the cover member, the second engagement portion being configured to be engaged with the first engagement portion,
   wherein the structure and the cover member include an operation guide portion in which a first state in which positions of the first engagement portion and the second engagement portion in a rotational direction are not coincident with each other is shifted to a third state in which the positions of the first engagement portion and the second engagement portion in the rotational direction are coincident with each other, via a second state through relative rotation,
   wherein the movement restriction unit includes:
   an attachment portion that is provided in one of the operation unit and the structure; and
   a sliding surface that is provided in the other one of the operation unit and the structure, extends in the axial direction, and is configured to slidably contact the attachment portion in the axial direction, wherein, in the first state, the attachment portion is positioned away from the sliding surface, wherein, in the second state, the attachment portion is configured to slide along the sliding surface while restricting the relative rotation between the operation unit and the structure and restricting the shift to the third state by bringing the attachment portion into contact with the sliding surface, and wherein the attachment portion sliding on the sliding surface is accommodated in an accommodation portion that is formed on a side in a movement direction of the attachment portion with respect to the sliding surface and is configured to receive the attachment portion such that the operation unit and the structure relatively rotate and enter the third state where the cover member is movable relative to the structure in the distal direction by the exposure restriction operation distance.

3. The liquid administration device according to claim 2, wherein a slope is formed in one of the operation unit and the structure, and a contact portion that is configured to contact the slope is formed in the other one of the operation unit and the structure, wherein the structure is configured to move relative to the operation unit in a proximal direction, and wherein the liquid administration device is configured such that the contact portion is movable along the slope by being brought into contact with the slope such that a state of the structure and the operation unit can be shifted from the second state to the third state.

4. The liquid administration device according to claim 2, wherein the operation guide portion includes a cam groove in one of the structure and the cover member, and a convex portion, which is accommodated in the cam groove and moves along the cam groove, in the other one of the structure and the cover member, wherein the cam groove includes:
 a first groove portion that is configured to allow relative movement between the structure and the cover member in the axial direction in the first state,
 a second groove portion that is configured to communicate with the first groove portion, is inclined in the axial direction, and is configured to allow relative rotation between the structure and the cover member so as to shift the state of the structure and the cover member from the first state to the third state, and
 a third groove portion that is configured to communicate with the second groove portion and is configured to allow engagement of the first engagement portion and the second engagement portion by relatively moving the structure and the cover member in the axial direction in the third state, and wherein, in the second state, the convex portion is positioned in the second groove.

5. The liquid administration device according to claim 4, wherein a holding portion for suspension is formed in the second groove, the holding portion for suspension being configured to make the convex portion movable in the axial direction in the second state by less than the exposure restriction operation distance.

6. The liquid administration device according to claim 5, wherein an edge for suspension is formed at an edge of the holding portion for suspension, wherein the edge for suspension is orthogonal to the axial direction or is inclined in an opposite direction to a direction in which the second groove is inclined in the axial direction, and wherein the edge for suspension is configured such that the convex portion is held in the second state when the convex portion is brought into contact with the edge for suspension.

7. The liquid administration device according to claim 6, wherein a slope is formed in one of the operation unit and the structure, and a contact portion configured to contact the slope is formed in the other of the operation unit and the structure, wherein the structure is configured to move relative to the operation unit in a proximal direction, and wherein the liquid administration device is configured such that the contact portion is moveable along the slope by being brought into contact with the slope such that the state of the structure and the operation unit can be shifted from the second state to the third state.

8. The liquid administration device according to claim 5, wherein the holding portion for suspension of the second groove is formed lengthwise in a stepped shape in the distal direction from the second groove.

9. The liquid administration device according to claim 8, wherein the holding portion for suspension is configured such that in the second state the cover member may move in the distal direction and cover the needle tube.

10. The liquid administration device according to claim 5, wherein the holding portion for suspension of the second groove is formed parallel to the third groove.

11. The liquid administration device according to claim 5, wherein a slope is formed in one of the operation unit and the structure, and a contact portion configured to contact the slope is formed in the other of the operation unit and the structure, wherein the structure is configured to move relative to the operation unit in a proximal direction, and wherein the liquid administration device is configured such that the contact portion is moveable along the slope by being brought into contact with the slope such that a state of the structure and the operation unit can be shifted from the second state to the third state.

12. The liquid administration device according to claim 4, wherein a slope is formed in one of the operation unit and the structure, and a contact portion which can come into contact with the slope is formed in the other of the operation unit and the structure, wherein the structure is configured to move relative to the operation unit in a proximal direction, and wherein the liquid administration device is configured such that the contact portion is moveable along the slope by being brought into contact with the slope such that a state of the structure and the operation unit can be shifted from the second state to the third state.

13. A liquid administration device for administering a liquid into a living body, comprising:
 a structure that includes an accommodation body configured to accommodate the liquid therein and a needle tube communicatable with an inside of the accommodation body;
 an operation unit configured to move in a distal direction with respect to the structure by a predetermined distance to a location at which administration of the liquid is completed;

a cover member that is movable between a protection position at which the needle tube is covered and an exposure position at which the needle tube is exposed;

a biasing member that biases the cover member in the digital direction, wherein the cover member is moveable from the exposure postition to the protection position via a biasing force of the biasing member;

an exposure restriction unit configured to restrict movement of the cover member to the exposure position when the cover member arrives at a predetermined exposure restriction operation distance; and a movement restriction unit configured not to restrict movement of the cover member to the exposure position until the cover member moves to the predetermined exposure restriction operation distance.

14. The liquid administration device according to claim 13, wherein the exposure restriction unit includes:
a first engagement portion that is formed in one of the structure and the cover member; and
a second engagement portion that is formed in the other one of the structure and the cover member, the second engagement portion being configured to be engaged with the first engagement portion, wherein the structure and the cover member include an operation guide portion in which a first state in which positions of the first engagement portion and the second engagement portion in a rotational direction are not coincident with each other is shifted to a third state in which the positions of the first engagement portion and the second engagement portion in the rotational direction are coincident with each other, via a second state through relative rotation, wherein the movement restriction unit includes:
an attachment portion that is provided in one of the operation unit and the structure; and
a sliding surface that is provided in the other one of the operation unit and the structure, extends in an axial direction, and is configured to slidably contact the attachment portion in the axial direction, wherein, in the first state, the attachment portion is positioned away from the sliding surface, wherein, in the second state, the attachment portion is configured to slide along the sliding surface while restricting the relative rotation between the operation unit and the structure and restricting the shift to the third state by bringing the attachment portion into contact with the sliding surface, and wherein the attachment portion sliding on the sliding surface is accommodated in an accommodation portion that is formed on a side in a movement direction of the attachment portion with respect to the sliding surface and is configured to receive the attachment portion such that the operation unit and the structure relatively rotate and enter the third state where the cover member is movable relative to the structure in the distal direction by the exposure restriction operation distance.

15. The liquid administration device according to claim 14, wherein a slope is formed in one of the operation unit and the structure, and a contact portion that is configured to contact the slope is formed in the other one of the operation unit and the structure, wherein the structure is configured to move relative to the operation unit in a proximal direction, and wherein the liquid administration device is configured such that the contact portion is movable along the slope by being brought into contact with the slope such that a state of the structure and the operation unit can be shifted from the second state to the third state.

16. The liquid administration device according to claim 14, wherein the operation guide portion includes a cam groove in one of the structure and the cover member, and a convex portion, which is accommodated in the cam groove and moves along the cam groove, in the other one of the structure and the cover member, wherein the cam groove includes:
a first groove that is configured to allow relative movement between the structure and the cover member in the axial direction in the first state,
a second groove that is configured to communicate with the first groove portion, is inclined in the axial direction, and is configured to allow relative rotation between the structure and the cover member so as to shift the state of the structure and the cover member from the first state to the third state, and
a third groove that is configured to communicate with the second groove portion and is configured to allow engagement of the first engagement portion and the second engagement portion by relatively moving the structure and the cover member in the axial direction in the third state, and wherein, in the second state, the convex portion is positioned in the second groove.

17. The liquid administration device according to claim 16, wherein a holding portion for suspension is formed in the second groove, the holding portion for suspension being configured to make the convex portion movable in the axial direction in the second state by less than the exposure restriction operation distance.

18. The liquid administration device according to claim 17, wherein an edge for suspension is formed at an edge of the holding portion for suspension, wherein the edge for suspension is orthogonal to the axial direction or is inclined in an opposite direction to a direction in which the second groove is inclined in the axial direction, and wherein the edge for suspension is configured such that the convex portion is held in the second state when the convex portion is brought into contact with the edge for suspension.

19. The liquid administration device according to claim 18, wherein a slope is formed in one of the operation unit and the structure, and a contact portion configured to contact the slope is formed in the other of the operation unit and the structure, wherein the structure is configured to move relative to the operation unit in a proximal direction, and wherein the liquid administration device is configured such that the contact portion is moveable along the slope by being brought into contact with the slope such that a state of the structure and the operation unit can be shifted from the second state to the third state.

20. The liquid administration device according to claim 17, wherein the holding portion for suspension of the second groove is formed lengthwise in a stepped shape in the distal direction from the second groove.

21. The liquid administration device according to claim 20, wherein the holding portion for suspension is configured such that in the second state the cover member may move in the distal direction and cover the needle tube.

22. The liquid administration device according to claim 17, wherein the holding portion for suspension of the second groove is formed parallel to the third groove.

23. The liquid administration device according to claim 17,
- wherein a slope is formed in one of the operation unit and the structure, and a contact portion configured to contact the slope is formed in the other of the operation unit and the structure,
- wherein the structure is configured to move relative to the operation unit in a proximal direction, and
- wherein the liquid administration device is configured such that the contact portion is moveable along the slope by being brought into contact with the slope such that a state of the structure and the operation unit can be shifted from the second state to the third state.

24. The liquid administration device according to claim 16,
- wherein a slope is formed in one of the operation unit and the structure, and a contact portion which can come into contact with the slope is formed in the other of the operation unit and the structure,
- wherein the structure is configured to move relative to the operation unit in a proximal direction, and
- wherein the liquid administration device is configured such that the contact portion is moveable along the slope by being brought into contact with the slope such that a state of the structure and the operation unit can be shifted from the second state to the third state.

* * * * *

UNITED STATES PATENT AND TRADEMARK OFFICE
CERTIFICATE OF CORRECTION

PATENT NO. : 10,086,152 B2
APPLICATION NO. : 14/641282
DATED : October 2, 2018
INVENTOR(S) : Masaomi Imai, Ruriko Iibuchi and Manabu Arinobe It is certified that error appears in the above-identified patent and that said Letters Patent is hereby corrected as shown below:

In the Claims

Claim 4, Column 29, Line 48:
Please delete "shift the state" and insert --shift a state--.

Claim 5, Column 29, Line 61:
Please delete "second grove" and insert --second grove portion--.

Claim 6, Column 30, Line 3:
Please delete "second grove" and insert --second grove portion--.

Claim 8, Column 30, Lines 23-25:
Please delete "suspension of the second groove is formed lengthwise in a stepped shape in the distal direction from the second groove" and insert --suspension of the second groove portion is formed lengthwise in a stepped shape in the distal direction from the second groove portion--.

Claim 10, Column 30, Lines 31-32:
Please delete "suspension of the second groove is formed parallel to the third groove" and insert --suspension of the second groove portion is formed parallel to the third groove portion--.

Claim 13, Column 31, Line 5:
Please delete "digital" and insert --distal--.

Claim 13, Column 31, Line 7:
Please delete "postition" and insert --position--.

Claim 16, Column 32, Line 16:
Please delete "first grove portion" and insert --first grove--.

Signed and Sealed this
Nineteenth Day of February, 2019

Andrei Iancu
*Director of the United States Patent and Trademark Office*

CERTIFICATE OF CORRECTION (continued)
U.S. Pat. No. 10,086,152 B2

Claim 16, Column 32, Line 19:
Please delete "shift the state" and insert --shift a state--.

Claim 16, Column 32, Line 22:
Please delete "second grove portion" and insert --second grove--.